(12) United States Patent
Leighton

(10) Patent No.: US 9,415,035 B2
(45) Date of Patent: Aug. 16, 2016

(54) COMPOSITIONS CONTAINING OMEGA-3 OIL WITH AN ANTI-INFLAMMATORY AGENT AND USES THEREOF

(75) Inventor: Harry J. Leighton, Rockport, ME (US)

(73) Assignee: Maine Natural Health Company, Inc., Warren, ME (US)

( * ) Notice: Subject to any disclaimer, the term of this patent is extended or adjusted under 35 U.S.C. 154(b) by 0 days.

(21) Appl. No.: 13/822,520

(22) PCT Filed: Sep. 15, 2011

(86) PCT No.: PCT/US2011/051734
§ 371 (c)(1),
(2), (4) Date: Nov. 6, 2013

(87) PCT Pub. No.: WO2012/037328
PCT Pub. Date: Mar. 22, 2012

(65) Prior Publication Data
US 2014/0050807 A1   Feb. 20, 2014

Related U.S. Application Data

(60) Provisional application No. 61/384,037, filed on Sep. 17, 2010.

(51) Int. Cl.
| | | |
|---|---|---|
| A01N 65/00 | (2009.01) | |
| A61K 31/232 | (2006.01) | |
| A61K 36/53 | (2006.01) | |
| A61K 45/06 | (2006.01) | |

(52) U.S. Cl.
CPC ............ *A61K 31/232* (2013.01); *A61K 36/53* (2013.01); *A61K 45/06* (2013.01)

(58) Field of Classification Search
CPC ..................................................... A61K 36/00
USPC ........................................................ 424/725
See application file for complete search history.

(56) References Cited

U.S. PATENT DOCUMENTS

| | | | |
|---|---|---|---|
| 5,130,242 | A | 7/1992 | Barclay |
| 5,780,039 | A | 7/1998 | Greenberg et al. |
| 6,121,470 | A | 9/2000 | Takahashi et al. |
| 6,284,268 | B1 | 9/2001 | Mishra et al. |
| 7,741,374 | B1 | 6/2010 | Arnold et al. |
| 2002/0044961 | A1 | 4/2002 | Kirschner et al. |
| 2003/0104048 | A1 | 6/2003 | Patel et al. |
| 2003/0161918 | A1 | 8/2003 | Kendrick et al. |
| 2005/0113449 | A1 | 5/2005 | Renshaw |
| 2005/0184275 | A1 | 8/2005 | Mora-Gutierrez et al. |
| 2005/0187204 | A1 | 8/2005 | Kondo et al. |
| 2006/0088574 | A1 | 4/2006 | Manning et al. |
| 2007/0104779 | A1 | 5/2007 | Rongen et al. |
| 2007/0141138 | A1 | 6/2007 | Feuerstein et al. |
| 2007/0253941 | A1 | 11/2007 | Naidu et al. |
| 2007/0269507 | A1 | 11/2007 | Sachetto et al. |
| 2008/0085320 | A1 | 4/2008 | Dror et al. |
| 2008/0268036 | A1 | 10/2008 | Guy et al. |
| 2009/0099261 | A1 | 4/2009 | Bell et al. |
| 2009/0149533 | A1 | 6/2009 | Almarsson et al. |
| 2009/0186096 | A1 | 7/2009 | Kritzman et al. |
| 2009/0215897 | A1 | 8/2009 | Beermann et al. |
| 2009/0297665 | A1 | 12/2009 | Bromley |
| 2010/0166918 | A1 | 7/2010 | Miller |
| 2010/0173876 | A1 | 7/2010 | Lichtenberger et al. |
| 2010/0197628 | A1 | 8/2010 | Renshaw et al. |

OTHER PUBLICATIONS

Bloomer et al., "Effect of eicosapentaenoic and docosahexaenoic acid on resting and exercise-induced inflammatory and oxidative stress biomarkers: a randomized, placebo controlled, cross-over study," *Lipids in Health and Disease*; 8(36): 1-12 (2009).
Fearon et al., "Double-blind, placebo-controlled, radomized study of eicosapentaenoic acid diester in patients with cancer cachexia," *Journal of Clinical Oncology*, 24(21): 3401-3407 (2008).
Schwalfenberg, "Omega-3 fatty acids: their beneficial role in cardiovascular health," *Can Fam Physician*, 52:734-740 (2006).
Takaki et al., "Anti-inflammatory and antinociceptive effects of *Rosmarinus officinalis* L. essential oil in experimental animal models," *Journal of Medicinal Food*, 11(4): 741-746 (2008).
International Preliminary Report on Patentability and Written Opinion for Internation Application No. PCT/US2011/051734, mailed Mar. 28, 2013.
International Preliminary Report on Patentability and Written Opinion for International Application No. PCT/US2011/051698, mailed Mar. 28, 2013.

*Primary Examiner* — Michael Meller
(74) *Attorney, Agent, or Firm* — Clark & Elbing LLP

(57) ABSTRACT

The invention provides compositions containing omega-3 oil and at least one anti-inflammatory agent and/or at least one gastrotoxic, nephrotoxic, or hepatotoxic pharmaceutical agent. The invention further provides kits containing these compositions and methods for decreasing pain or inflammation, decreasing the symptoms of an allergic condition, and/or the gastrotoxicity, nephrotoxicity, and hepatotoxicity of a pharmaceutical agent in a subject (e.g., a human) or companion animal requiring the administration of at least one composition containing omega-3 oil. The invention also provides methods for formulating an anti-inflammatory agent to increase its absorption rate requiring the mixing of omega-3 oil with the anti-inflammatory agent and methods of concentrating an omega-3 oil.

7 Claims, No Drawings

US 9,415,035 B2

COMPOSITIONS CONTAINING OMEGA-3 OIL WITH AN ANTI-INFLAMMATORY AGENT AND USES THEREOF

CROSS REFERENCE TO RELATED APPLICATIONS

This application is the U.S. National Stage of International Application No. PCT/US2011/051734, filed Sep. 15, 2011, which claims benefit of U.S. Provisional Application No. 61/384,037, filed Sep. 17, 2010, each of which is hereby incorporated by reference.

FIELD OF THE INVENTION

The present invention relates to the field of pharmacology and molecular medicine. More specifically, the invention relates to pharmaceutical compositions containing omega-3 oil in combination with an anti-inflammatory agent or a pharmaceutical agent that induces gastrotoxicity, nephrotoxicity, or hepatotoxicity. The invention further relates to methods of reducing pain, inflammation, allergic symptoms, gastrotoxicity, nephrotoxicity, or hepatotoxicity by administering these compositions to subjects and companion animals.

BACKGROUND OF THE INVENTION

A variety of anti-inflammatory medications are prescribed to counteract pain and inflammation associated with a variety of disease states (e.g., rheumatoid arthritis). Commonly prescribed anti-inflammatory medications are generally divided into two mechanism-based groups: cyclooxygenase (COX)-1 inhibitors and COX-2 inhibitors. COX-1 inhibitors, as a class, induce gastric irritation when administered in commercial tablet or capsule dosage forms. COX-2 inhibitors cause much less gastric irritation, but may not affect platelet aggregation to the same extent as COX-1 inhibitors. Additional anti-inflammatory medications include disease-modifying anti-rheumatic drugs (DMARDs) (e.g., methotrexate and dihydrofolate inhibitors), agents that block, absorb, or eliminate excessive tumor necrosis factor (TNF)-α expression or activity, and/or agents that have as a part of their pharmacology an anti-histamine activity (e.g., an H-1 antihistamine).

A variety of medications, while demonstrating efficacy in treating or ameliorating the symptoms of a disease, have a side effect of gastrotoxicity, nephrotoxicity, or hepatotoxicity. For example, several non-steroidal anti-inflammatory drugs (NSAIDs) have been shown to induce gastrotoxicity, nephrotoxicity, or hepatotoxicity following sustained use. As a variety of disease states in humans involve inflammation and/or pain, additional and, preferably, enhanced anti-inflammatory agents and therapies are desired. In fact, virtually all chronic diseases have a component (co-morbidity) of inflammation that sustains and in some cases increases the symptoms of the disease state.

Omega-3 oils have been generally accepted by the health care community as a dietary supplement for the treatment of heart disease and hyperlipidemia. The dose strength and formulation for omega-3 oil required for optimal clinical benefit has yet to be fully defined, but initial studies indicate that the dose necessary to achieve a health benefit was less than 3 grams per day. The American Heart Association recommended dose is 1.0 gram a day and the Food and Drug Administration recommends a maximum daily consumption of omega-3 oil of less than 3.0 grams a day. Omega-3 oils have also been reported to have anti-inflammatory activity. However, the published results regarding this activity are variable and inconsistent. For example, one study reported that administration of omega-3 oil in a dosage of 8 grams a day for 5 months results in a 33-68% decrease in inflammation (Kremer et al., *Arthritis Rheum.*, 38:1107-1114, 1995). In contrast, another study reported that the administration of 2.1 grams of omega-3 oil a day for 8 months mediated only a 12-17% reduction in inflammation (Adam et al., *Rheumatoid Int.* 23:27-36, 2003). Further studies using gel cap formulations of omega-3 oil in varying dosage strengths were inconclusive or negative. New studies with optimal formulations are required to understand the medical value of omega-3 oil alone and in combination with modern therapeutics.

This patent teaches the use of high dose (greater than 3.0 grams/day) liquid omega-3 oils as an anti-inflammatory therapy. It is difficult to ingest enough gel capsules to achieve this dosage. Compliance and swallowing difficulties limit the ability of many patients to consistently take an amount of omega-3 oil sufficient to elicit an anti-inflammatory effect.

In view of the large number of diseases that involve inflammation and pain, additional anti-inflammatory therapies are desired, and preferably, such therapies do not have negative side effects, such as drug-induced gastrotoxicity, nephrotoxicity, or hepatotoxicity.

SUMMARY OF THE INVENTION

In a first aspect, the invention provides compositions containing an omega-3 oil and at least one anti-inflammatory agent. In various embodiments, these compositions are formulated as a liquid (e.g., formulated as a liquid for oral administration). In additional embodiments, the compositions further contain at least one absorption enhancer. The omega-3 oil in the provided compositions may be from a natural source (e.g., salmon, herring, mackerel, and sardines), may be an alkyl ester of a fatty acid (e.g., an alkyl ester of EPA or DHA), a mixture of EPA and DHA, may be in the form of triglycerides, a mixture of triglycerides and free fatty acids, and/or may be high grade (e.g., OmegaMaine omega-3 oils). The provided compositions may be formulated in a dose (e.g., as a liquid) containing greater than 3.0 g combined EPA and DHA (e.g., formulated in a liquid dose containing greater than 3.0 g combined EPA and DHA per 10 mL).

The absorption enhancers used in the above compositions may contain at least one non-hydrophilic surfactant or solvent. The anti-inflammatory agents used in the above compositions may be water insoluble, have a melting point below 200° C., a log P value greater than 3, or may induce gastrotoxicity, nephrotoxicity, or hepatotoxicity when administered alone to a subject. The anti-inflammatory agents used in the above compositions may be a natural anti-inflammatory agent (e.g., a herbal-based oil (e.g., an extract of basil, rosemary (e.g., rosemary oil), turmeric, or ginger, glucosamine, or bromelin). In various embodiments of the provided compositions, a herbal-based oil may represent 0.5% to 5% of the composition's total mass.

The anti-inflammatory agents included in the compositions of the invention may be a cyclooxygenase (COX)-1 inhibitor (e.g., diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, oxaprozin, piroxicam, salsalate, sulindac, and tolmetin), a COX-2 inhibitor (e.g., celecoxib and valdecoxib), a disease-modifying anti-inflammatory drug (DMARD) (e.g., auranofin, aurothioglucose, azathioprine, chlorambucil, cyclophosphamide, D-penicillamine, gold sodium thiomalate (injectible gold), hydroxychloroquine, leflunomide, methotrexate, minocycline, mycophenolate, and sulfasalazine), a steroid, a tumor necrosis factor (TNF)-α inhibitor (e.g., thalidomide, lenalidomide, etanercept, pegsunercept, bupropion, and pentoxifylline), an antihistamine (e.g., a tricyclic antihistamine, such as doxepin and impramine, or a non-tricyclic antihistamine, such as diphenhydramine or triprolidine).

In any of the above embodiments, the absorption enhancer may be ethanol, vitamin E, a polyethylene glycol, a Tween surfactant, cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides (MCTs), sodium lauryl sulfate, natural fish oil, palmitic monoglycerides or diglycerides, capric monoglycerides or diglycerides, amides of intermediate (C-8 to C-12) fatty acids, and amides of long chain (C-13 to C-24) fatty acids. In additional examples of the compositions, the amides of the intermediate fatty acids and the amides of the long chain fatty acids may be derived from a naturally-occurring amino acid (e.g., alanine, lysine, and glycine). In additional embodiments of the above compositions, the absorption enhancer is vitamin E and the anti-inflammatory agent is rosemary oil. In further embodiments of the above compositions, the absorption enhancer is vitamin E and the amount of vitamin E present in a single dose of the composition is between 13.4 mg and 134 mg. In additional examples of the above compositions, the absorption enhancer does not exceed 30% of the composition's total mass. In yet further examples of these compositions, the absorption enhancer is selected from natural fish oil, palmitic monoglycerides or diglycerides, and capric monoglycerides or diglycerides.

In all the above compositions, the omega-3 oil may be between 60% to 80% of the composition's total mass or the anti-inflammatory agent may be between 0.1% to 20% of the composition's total mass. In additional embodiments of the compositions, the anti-inflammatory agent may be dissolved in a solution containing ethanol. Further embodiments of the compositions contain a mixture of at least one agent from the group of: phosphatidylinositol, phosphatidylserine, phosphatidylcholine, phosphatidylethanolamine, and phosphatidic acid that represents 1% to 10% of the composition's total mass. In additional embodiments, the compositions contains a mixture of phosphatidylcholine, phosphatidylserine, and phosphatidic acid that represents 1% to 10% of the composition's total mass.

In further embodiments of the above compositions, polytocopherol is 1% to 5% of the composition's total mass, arginine or citrulline is 1% to 5% of the composition's total mass, or MCTs are 1% to 10% of the composition's total mass. In desirable embodiments of the above compositions, the omega-3 oil and the anti-inflammatory agent are present in amounts sufficient to result in a synergistic decrease in at least one symptom of inflammation or a syngergistic decrease in at least one pain test score in a subject or patient population. In other desirable embodiments of the above compositions, the omega-3 oil or the anti-inflammatory agent is present in an amount sufficient to result in a decrease in at least one symptom of inflammation or a decrease in at least one pain test score in a subject or patient population (e.g., a composition formulated as a liquid or a composition wherein the omega-3 oil represents at least 50% (e.g., at least 70%) by volume of the composition). In additional desirable embodiments of the composition, the omega-3 oil and the anti-inflammatory agent are present in amounts sufficient to reduce the dosage of coumadin or warfarin administered to a subject having an increased risk of having a stroke.

Additional examples of the above compositions contain by weight: 60% to 80% omega-3 oil; 0.5% to 5% rosemary oil; 1% to 10% mixture of phosphatidylserine, phosphatidylcholine, and phosphatidic acid; 1% to 5% polytocopherol; 1% to 5% arginine or citrulline; and 1% to 10% MCTs. Further examples of the above compositions contain by weight: 60% to 80% omega-3 oil; 0.5% to 5% rosemary oil; 1% to 10% mixture of phosphatidylserine, phosphatidylcholine, and phosphatidic acid; 1% to 5% polytocopherol; 1% to 5% arginine or citrulline; and 1% to 20% anti-inflammatory agent.

The invention further provides kits containing at least one of the above compositions and instructions for administering the composition(s) to a subject. In certain embodiments of these kits, the compositions are administered to a subject having dysphagia. In additional embodiments of the provided kits, the composition has an increased rate of absorption or decreased variability in absorption rate as compared to the rate of absorption and the variability of absorption observed for a solid oral formulation of the anti-inflammatory agent alone. The above kits may further include at least one additional composition containing an anti-inflammatory agent (e.g., a NSAID, a DMARD, or an antihistamine (e.g., a tricyclic antihistamine, such as doxepin or impramine, or a non-tricyclic antihistamine, such as diphenhydramine or triprolidine). In additional embodiments of the above kits, the composition and the at least one additional composition are formulated as a liquid (e.g., a liquid for oral administration) and/or are administered to a subject having dysphagia.

The invention also provides methods of decreasing pain (e.g., chronic pain, neuropathic pain, or acute pain) or at least one symptom of inflammation in a subject requiring the step of administering to a subject at least one of the above compositions. In additional embodiments of these methods, the compositions are formulated as a liquid (e.g., a liquid for oral administration). In further embodiments of these methods, the composition is administered once a day (e.g., orally administered once a day). Desirably, the above methods result in at least a 5% reduction in a pain test score, at least a 5% reduction in cyclooxygenase (COX)-1 and/or COX-2 activity, at least a 5% reduction in white blood cell count, at least a 5% reduction in C-reactive protein levels, at least a 5% reduction in interleukin-6 levels, and/or at least a 5% reduction in TNF-α levels in the subject. Additional desirable embodiments of the above methods result in at least a 2-fold decrease in the time to optimal therapeutic effect.

The above methods may further include administering to the subject at least one additional composition containing an anti-inflammatory agent (e.g., a NSAID, a DMARD, or an antihistamine). In additional embodiments of the above methods, the composition and the at least one additional composition are formulated in a liquid (e.g., a liquid for oral administration) and/or are administered to a subject having dysphagia. Desirable embodiments of these method result in a syngeristic decrease in at least one symptom of inflammation or a syngergistic decrease in at least one test pain score in the subject compared to the sum of the effect of the omega-3 oil alone and the effect of the anti-inflammatory agent(s) alone on the symptom(s) of inflammation or the test pain score(s) in a subject or patient population. In additional embodiments of the above methods, the pain or inflammation is associated with cancer, viral infection, rheumatoid arthritis, osteoarthritis, Crohn's disease, liver disease, inflammatory heart disease, kidney disease, gastritis, gingivitis, periodontal disease, asthma, chronic obstructive pulmonary disease, autoimmune disease, irritable bowel syndrome, fibromyalgesia, leg pains, restless leg syndrome, diabetic neuropathy, or an allergic condition.

The invention further provides method of reducing at least one symptom of an allergic condition (e.g., allergen-induced dermatitis, rhinitis, or seasonal allergies) in a subject requiring the step of administering at least one of the above described compositions containing an omega-3 oil and at least one anti-inflammatory agent to a subject. In various embodiments of this method, the composition is formulated as a liquid (e.g., formulated as a liquid for oral administration). In additional embodiments of the above methods, the composition is administered once a day (e.g., administered orally once a day). Additional embodiments of the above methods may further include administering to the subject at least one additional composition containing an anti-inflammatory agent (e.g., an antihistamine (e.g., a tricyclic antihistamine, such as doxepin or impramine, or a non-tricyclic antihistamine, such as diphenydramine and triprolidine), a NSAID, or a DMARD). In further embodiments of the above methods, the composition and the at least one additional composition may be formulated in a liquid (e.g., formulated in a liquid for oral administration) and/or administered to a subject having dysphagia. In additional embodiments of the above methods, the one or more symptoms of an allergic condition is selected from the group of nasal congestion, sneezing, runny nose, watery eyes, swollen eyes, itchy nose, itchy skin, itchy eyes, tingling mouth, swelling of the lips, mouth, or throat, hives, anaphylaxis, rash, and wheezing. Desirable embodiments of the above methods result in a synergistic decrease in one or more symptoms of an allergic condition compared to the sum of the effects of the omega-3 oil and the anti-inflammatory agent on the one or more symptoms when administered alone.

The invention also provides methods of decreasing at least one symptom of inflammation or at least one symptom of an allergic condition (e.g., allergen-induced dermatitis, rhinitis, or seasonal allergies) in a companion animal (e.g., a dog, a cat, a bird, or a horse) requiring the step of administering to the animal at least one composition containing an omega-3 oil and at least one anti-inflammatory agent (e.g., any of the compositions described above). In additional embodiments of these methods, the composition is formulated as a liquid (e.g., formulated as a liquid for oral administration or formulated as a liquid composition to be added to the companion animal's normal food source (e.g., dry food composition)). In further embodiments of the above methods, the composition is administered once a day (e.g., orally administered once a day). Additional embodiments of the above methods further require administering to the animal at least one additional composition containing an anti-inflammatory agent (e.g., an antihistamine (e.g., a tricyclic antihistamine, such as doxepin and impramine, or a non-tricyclic antihistamine, such as diphendramine and triprolidine), a DMARD, or a NSAID). In further embodiments of the above methods, the composition and the at least one additional composition are formulated in a liquid (e.g., formulated in a liquid for oral administration) and/or are administered to an animal having dysphagia.

In any of the above methods, the one or more symptoms of an allergic condition may be selected from the group of: nasal congestion, sneezing, runny nose, watery eyes, swollen eyes, itchy nose, itchy skin, itchy eyes, tingling mouth, swelling of the lips, mouth, or throat, hives, anaphylaxis, rash, wheezing, loss of or a decrease in mobility, and increased sleeping. Desirable embodiments of the above methods result in a syngeristic decrease in one or more symptoms of an allergic condition or inflammation compared to the sum of the effects of the omega-3 oil and the anti-inflammatory agent on the one or more symptoms when administered alone. In additional embodiments of the above methods, the composition contains glucosamine or contains glucosamine and at least one antihistamine. Additional desirable embodiments of the above methods result in at least a 5% reduction in COX-1 and/or COX-2 activity, at least a 5% reduction in white blood cell count, at least a 5% reduction in C-reactive protein levels, at least a 5% reduction in interleukin-6 levels, or at least a 5% reduction in TNF-α levels in the animal.

The invention further provides methods of decreasing at least one symptom of inflammation or decreasing at least one pain test score in a subject requiring the step of administering to a subject a first composition containing an omega-3 oil (e.g., any of the omega-3 oil compositions describe above) and a second composition containing at least one anti-inflammatory agent, wherein the administering results in a synergistic decrease in at least one symptom of inflammation or a synergistic decrease in at least one pain test score in the patient compared to the sum of the effect of the first composition alone and the effect of the second composition alone on the symptom(s) of inflammation or the test pain score(s) in a subject or patient population. In any of these methods, the first composition and/or second composition may be formulated as a liquid (e.g., a liquid for oral administration). In additional embodiments of these methods, the omega-3 oil in the first composition may be from a natural source (e.g., salmon, herring, mackerel, and sardines), may be an alkyl ester of a fatty acid (e.g., an alkyl ester of EPA and DHA), a mixture of EPA and DHA, may be in the form of triglycerides, may be a mixture of triglycerides and free fatty acids, and/or may be high grade (e.g., OmegaMaine omega-3 oils). In additional embodiments of the above methods, the first composition may contain at least one absorption enhancer.

In additional embodiments of these methods, the first composition and/or the second composition are administered once a day (e.g., orally administered). In additional embodiments of the above methods, the subject may have dysphagia. In other embodiments of the above methods, the first composition is administered in a dose containing greater than 3.0 g combined EPA and DHA (e.g., administered in a dose containing greater than 3.0 g combined EPA and DHA per 10 mL). Desirably, the methods result in at least a 5% reduction in pain score, at least a 5% reduction in COX-1 and/or COX-2 activity, at least a 5% reduction in white blood cell count, at least a 5% reduction in C-reactive protein levels, at least a 5% reduction in interleukin-6 levels, and/or at least a 5% reduction in TNF-α levels in the subject. Additional desirable embodiments of the above methods result in at least a 2-fold decrease in the time to optimal therapeutic effect. In additional embodiments of the above methods, the anti-inflammatory agent may be a natural inflammatory agent (e.g., glucosamine, bromelin, a herbal-based oil (e.g., an extract of basil, rosemary, turmeric, or ginger), a COX-1 inhibitor (e.g., diclofenac, diflunisal, etodolac, fenoprofen, flubiprofen, ibuprofen, indomethacin, ketoprofen, ketorolac, meclofenamate, mefenamic acid, meloxicam, nabumetone, naproxen, oxaprozin, piroxicam, salsalate, sulidac, and tolmetin), a COX-2 inhibitor (e.g., celecoxib and valdecoxib), a DMARD (e.g., auranofin, aurothioglucose, azathioprine, chlorambucil, cyclophosphamide, D-penicillamine, gold sodium thiomalate (injectible gold), hydroxychloroquine, leflunomide, methotrexate, minocycline, mycophenolate, and sulfasalazine), a steroid, a TNF-α inhibitor (e.g., thalidomide, lenalidomide, etanercept, pegsunercept, bupropion, and pentoxifylline), or an antihistamine (e.g., a tricyclic antihistamine, such as doxepin and imipramine, or a non-tricyclic antihistamine, such as diphenhydramine and triprolidine).

In additional embodiments of all the above methods, the first composition and the second composition are co-administered to the subject. In further embodiments of the above methods, the first composition is administered to the subject prior to the administration of the second composition to the subject or the second composition is administered to the subject prior to the administration of the first composition to the subject. In additional embodiments of the above methods, the pain is chronic pain, neuropathic pain, or acute pain, or the pain or inflammation is associated with cancer, viral infection, rheumatoid arthritis, osteoarthritis, Crohn's disease, liver disease, inflammatory heart disease, kidney disease, gastritis, gingivitis, periodontal disease, asthma, chronic obstructive pulmonary disease, autoimmune disease, irritable bowel syndrome, fibromyalgesia, leg pain, restless leg syndrome, neuropathic pain, diabetic neuropathy, or an allergic condition.

The invention also provides methods of decreasing at least one symptom of gastrotoxicity, nephrotoxicity, or hepatotoxicity (e.g., increased alanine aminotransferase levels in the blood, increased aspartate aminotransferase levels in the blood, increased gamma-glutamyltransferase levels in the blood, nausea, vomiting, abdominal pain, stomach pain, occult blood in feces, loss of appetite, diarrhea, weakness, jaundice, hepatomegaly, increased urea nitrogen in the blood, and increased creatine levels in urine) induced by at least one pharmaceutical agent in a subject requiring the step of administering: (i) at least one composition containing omega-3 oil, and (ii) at least one pharmaceutical agent to the subject, wherein the administering results in at least a 10% decrease in the symptom(s) of gastrotoxicity, nephrotoxicity, or hepatotoxicity observed when the pharmaceutical agent(s) are administered alone. In additional embodiments of these methods, the composition containing omega-3 oil is formulated as a liquid (e.g., formulated as a liquid for oral administration). In further embodiments of the above methods, the omega-3 oil in the compositions containing omega-3 oil may be from a natural source (e.g., salmon, herring, mackerel, and sardines), may be an alkyl ester of a fatty acid (e.g., an alkyl ester of EPA or DHA), a mixture of EPA and DHA, may be in the form of triglycerides, may be a mixture of triglycerides and free fatty acids, and/or may be high grade (e.g., OmegaMaine omega-3 oil). In additional examples of the above methods, the composition containing omega-3 oil may further contain at least one absorption enhancer. In further embodiments of the above methods, the composition containing omega-3 oil is administered once a day (e.g., orally administered once a day) and/or is administered in a dose containing greater than 3.0 g combined EPA and DHA (e.g., administered in a dose containing greater than 3.0 g combined EPA and DHA per 10 mL).

In additional embodiments of the above methods, the pharmaceutical agent is a NSAID, acetaminophen, ibuprofen, alpha-methyldopa, amiodarone, carbamazapine, chlorzoxazone, dantrolene, diclofenac, fluconazole, ketoconazole, flutamide, hydralazine, ibuprofen, imuran, azathioprine, isoniazid, ketek, long-acting nicotinic acid, zafirlukast accolade, zileuton, methotrexate, nitrofurantoin, perihexilene maleate, phenylbutazone, phenytoin, pravastin, fluvastatin, simavastatin, lovastatin, quinidine, rifampin, septra, bactrim, tacrine, tasmar, ticlid, troglitzone, clofarabine, pemetrexed, aldesleukin, fenofibrate, gemfibrozil, clofibrate, fenofibric acid, indomethacin, methotrexate sodium, ibuprofen, naproxen sodium, meloxicam, stavudine, didanosine, zidovudine, nevirapine, ritonavir, cisplatin, carboplatin, carmustine, mitomycin, amphotericin B, gentamycin, vancomycin, angiotensin-converting enzyme (ACE) inhibitors, furosemide, an HDL/LDL- or triglyceride-modifying drug (e.g., statins, niacin, niacin derivatives, and fibrates (e.g., fibric acid and fenofibrate), or an antihistamine (e.g., a tricyclic antihistamine, such as doxepin and imipramine, or a non-tricyclic antihistamine, such as dephenhydramine or triprolidine). In additional embodiments of the above methods, the composition containing omega-3 oil is administered to the subject prior to administering the pharmaceutical agent to the subject or the pharmaceutical agent is administered to the subject prior to administering the composition containing omega-3 oil to the subject.

In an additional aspect, the invention provides compositions containing an omega-3 oil and at least one gastrotoxic, nephrotoxic, or hepatotoxic pharmaceutical agent, wherein the omega-3 oil and the gastrotoxic, nephrotoxic, or hepatotoxic pharmaceutical agent are present in amounts sufficient to reduce the gastrotoxicity, nephrotoxicity, or hepatotoxicity of the pharmaceutical agent(s). These compositions may be formulated as a liquid (e.g., a liquid for oral administration) or may contain at least one absorption enhancer. The omega-3 oil in any of these compositions may be from a natural source (e.g., salmon, herring, mackerel, and sardines), may be an alkyl ester of a fatty acid (e.g., an alkyl ester of EPA or DHA), a mixture of EPA or DHA, may be in the form of triglycerides, may be a mixture of triglycerides and free fatty acids, and/or may be high grade (e.g., OmegaMaine omega-3 oils). In additional embodiments, the composition is formulated in a dose containing greater than 3.0 g combined EPA and DHA (e.g., formulated in a dose containing greater than 3.0 g combined EPA and DHA per 10 mL). Any of the above compositions, may contain an absorption enhancer that contains at least one non-hydrophilic surfactant or solvent. In additional embodiments of these compositions, the pharmaceutical agent may be water soluble, have a melting point below 200° C., and/or a log P value of greater than 3. In further embodiments of these compositions, the absorption enhancer may be selected from ethanol, vitamin E, a polyethylene glycol, a Tween surfactant, cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides (MCTs), sodium lauryl sulfate, natural fish oil, palmitic monoglycerides or diglycerides, capric monoglycerides or diglycerides, amides of intermediate (C-8 to C-12) fatty acids, and amides of long chain (C-13 to C-24) fatty acids. In additional embodiments of the above compositions, the amount of vitamin E present in a single dose of the composition is between 13.4 mg to 134 mg. In further embodiments of the above compositions, the absorption enhancer does not exceed 30% of the composition's total mass or the omega-3 oil is 60% to 80% of the composition's total mass.

In further embodiments of these compositions, the absorption enhancer is selected from the group of natural fish oil, palmitic monoglycerides or diglycerides, and capric monoglycerides, and diglycerides. In additional embodiments of the above compositions, the pharmaceutical agent is 0.1% to 20% of the composition's total mass or the pharmaceutical agent is dissolved in a solution containing ethanol. In further examples of the above compositions, a mixture of at least one agent from the group of phosphatidylinositol, phosphatidylserine, phosphatidylcholine, phosphatidylethanolamine, and phosphatidic acid is 1% to 10% of the composition's total mass (e.g., a mixture of phosphatidylcholine, phosphatidylserine, and phosphatidic acid). In additional examples of the above compositions, polytocopherol is 1% to 5% of the composition's total mass, arginine or citrulline is 1% to 5% of the composition's total mass, and/or MCTs are 1% to 10% of the composition's total mass.

In additional embodiments of the above compositions, the pharmaceutical agent is a NSAID, acetaminophen, ibuprofen, alpha-methyldopa, amiodarone, carbamazapine, chlorzoxazone, dantrolene, diclofenac, fluconazole, ketoconazole, flutamide, hydralazine, ibuprofen, imuran, azathioprine, isoniazid, ketek, long-acting nicotinic acid, zafirlukast accolade, zileuton, methotrexate, nitrofurantoin, perihexilene maleate, phenylbutazone, phenytoin, pravastin, fluvastatin, simavastatin, lovastatin, quinidine, rifampin, septra, bactrim, tacrine, tasmar, ticlid, troglitzone, clofarabine, pemetrexed, aldesleukin, fenofibrate, gemfibrozil, clofibrate, fenofibric acid, indomethacin, methotrexate sodium, ibuprofen, naproxen sodium, meloxicam, stavudine, didanosine, zidovudine, nevirapine, ritonavir, cisplatin, carboplatin, carmustine, mitomycin, amphotericin B, gentamycin, vancomycin, angiotensin-converting enzyme (ACE) inhibitors, furosemide, an antihistamine (e.g., a tricyclic antihistamine, such as doxepin or impramine, or a non-tricyclic antihistamine, such as diphenhydramine or triprolidine), or an HDL/LDL- or triglyceride-modifying drug (e.g., statins, niacin, niacin derivatives, and fibrates (e.g., fibric acid or fenofibrate).

Desirably, the omega-3 oil and the pharmaceutical agent(s) are present in amounts sufficient to reduce by at least 10% the severity or duration of at least one symptom of gastrotoxicity, nephrotoxicity, or hepatotoxicity (e.g., increased alanine aminotransferase levels in the blood, increased aspartate aminotransferase levels in the blood, increased gamma-glutamyltransferase levels in the blood, nausea, vomiting, abdominal pain, loss of appetite, diarrhea, weakness, jaundice, hepatomegaly, increased urea nitrogen in the blood, and increased creatine levels in urine) in a subject relative to the severity or duration of the symptoms in a subject receiving the pharmaceutical agent(s) alone (e.g., a composition formulated as a liquid or a composition wherein omega-3 oil represents at least 50% (e.g., at least 70%) of the volume of the composition). Examples of the above compositions contain by weight: 60% to 80% omega-3 oil; 0.5% to 5% rosemary oil; 1% to 10% mixture of phosphatidylserine, phosphatidylcholine, and phosphatidic acid; 1% to 5% polytocopherol; 1% to 5% arginine or citrulline; and 1% to 20% pharmaceutical agent.

The invention further provides kits containing at least one of the above compositions that contain an omega-3 oil and at least one gastrotoxic, nephrotoxic, or hepatotoxic pharmaceutical agent. Desirably, these kits contain a composition formulated as a liquid (e.g., a liquid formulated for oral administration). Any of the above embodiments of the kits, the composition may be administered to a subject having gastrotoxicity, hepatotoxicity, or dysphagia.

In a further aspect, the invention provides methods of formulating at least one anti-inflammatory agent to increase absorption rate requiring the step of mixing an omega-3 oil with at least one anti-inflammatory agent. In additional embodiments of this method, the omega-3 oil may be from a natural source (e.g., salmon, herring, mackerel, and sardines), may be an alkyl ester of a fatty acid (e.g., an alkyl ester of EPA or DHA), a mixture of EPA and DHA, may be in the form of triglycerides, may be a mixture of triglycerides and free fatty acids, and/or may be high grade (e.g., OmegaMaine omega-3 oil). Additional embodiments of these methods further include the step of adding at least one absorption enhancer (e.g., ethanol, vitamin E, polyethylene glycols, a Tween surfactant, cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides, sodium lauryl sulfate, natural fish oil, palmitic monoglycerides or diglycerides, capric monoglycerides or diglycerides, amides of intermediate (C-8 to C-12) fatty acids, and amides of long chain (C-13 to C-24) fatty acids). In further embodiments of the above methods, the at least one anti-inflammatory agent is first combined with at least one absorption enhancer to solubilize the at least one anti-inflammatory agent, and then the omega-3 oil is added to form the pharmaceutical composition. In additional embodiments of the above methods, the co-solvent contains ethanol.

The invention additionally provides methods for concentrating an omega-3 oil requiring the steps of: (a) decreasing the temperature of an omega-3 oil from 38° F. to 36° F., and incubating the oil at 36° F. between 1 hour to 24 hours, wherein the incubation at 36° F. results in the precipitation of high molecular weight lipids; (b) recovering the liquid phase in step (a); (c) decreasing the temperature of the recovered liquid phase in step (b) from 36° F. to 34° F.; (d) incubating the liquid in step (c) at 34° F. for 24 hours to 36 hours, wherein the 34° F. incubation results in the formation of a clarified liquid; and (3) recovering the clarified liquid, wherein the clarified liquid contains concentrated omega-3 oil and has a density less than the original omega-3 oil. In additional examples of these methods, the recovery in step (a) or step (e) may further comprise the step of centrifugation. In further embodiments, the above methods yield an omega-3 oil that is concentrated by at least 20% (e.g., by at least 40%).

By the term "omega-3 oil" is meant an oil that contains at least one (e.g., one, two, or three) fatty acid(s) containing a carbon-carbon double bond in the n-3 position (i.e., the third bond from the methyl end of the fatty acid). Non-limiting examples of fatty acids that may be present in an omega-3 oil include: all-cis-7,10,13-hexadecatrienoic acid; α-linolenic acid (ALA) (all-cis-9,12,15-octadecatrienoic acid); stearidonic acid (SDA) (all-cis-6,9,12,15-octadecatetraenoic acid); eicosatrienoic acid (ETE) (all-cis-11,14,17-eicosatrienoic acid); eicosatetraenoic acid (ETA) (all-cis-8,11,14,17-eicosatetraenoic acid); eicosapentaenoic acid (EPA) (all-cis-5,8,11,14,17-eicosapentaenoic acid); docosapentaenoic acid (DPA) (all-cis-7,10,13,16,19-docosapentaenoic acid); docosahexaenoic acid (DHA) (all-cis-4,7,10,13,16,19-docosahexaenoic acid); tetracosapentaenoic acid (all-cis-9,12,15,18,21-tetracosapentaenoic acid); and tetracosahexaenoic acid (nisinic acid) (all-cis-6,9,12,15,18,21-tetracosahexaenoic acid). The term "omega-3 oil" also includes omega-3 fatty acids in the form of free acids or incorporated as a part of a monoglyceride, diglyceride, or triglyceride, where at least one omega-3 fatty acid is incorporated as a fatty acid ester. The term "omega-3 oil" also includes the amides derived from omega-3 fatty acids. For example, amides of omega-3 fatty acids may be derived from naturally-occurring amino acids (e.g., glycine, lysine, and alanine).

Natural sources of omega-3 oils include, but are not limited to, cold water oily fish (e.g., salmon, tuna, herring, mackerel, anchovies, and sardines), pollock, cod, catfish, flounder, grouper, halibut, mahi mahi, orange roughy, red snapper, shark, swordfish, tilefish, plankton, algae, krill, green-lipped mussel, chia seeds, kiwifruit seeds, perilla seeds, flax seeds, lingonberry seeds, camelina seeds, purslane seeds, black raspberry seeds, hemp seeds, butternut, walnuts, pecan nuts, and hazel nuts. Omega-3 oil may also be synthesized in the form of alky esters (e.g., as in the commercial product Omacor or Lovaza).

By the term "herbal-based oil" is meant an oil extracted from a herb plant (e.g., rosemary, basil, turmeric, and ginger). The herbal-based oil may inhibit cyclooxgenase (COX)-1 or COX-2 activity (e.g., mediate at least a 5%, 10%, 15%, 20%, 25%, 30%, 35%, 40%, 45%, 50%, 60%, 70%, 80%, 90%, or 95% decrease in COX-1 and/or COX-2 activity). These oils contain multiple low potency inhibitors of cyclooxygenase. These inhibitors have additive and synergistic functions. The natural inhibitors bind to a variety of sites on the COX-1 and/or COX-2 surface and affect the function of these enzymes. Together, their combined activity is synergistic. Some of these inhibitors bind to the same sites on the COX-1 and/or COX-2 enzyme(s). In these instances, the inhibition is additive. A herbal extract may contain hundreds to thousands of COX-1 and/or COX-2 inhibitory molecules.

By the term "high grade omega-3 oil" is meant an omega-3 oil preparation that is substantially free of impurities (e.g., at least 70%, 75%, 80%, 85%, 90%, 95%, 96%, 97%, 98%, or 99% pure). For example, a high grade omega-3 oil may be purified to remove vitamin A, vitamin D, mercury, lead, polychlorinated biphenyls, dioxins, and excess fat by molecular distillation or by decreasing the temperature to affect the separation of non-omega-3 long chain fatty acids and oils from the omega-3 oils (as described herein).

By the term "Tween surfactant" is meant a nonionic detergent derived in part from polyethoxylated sorbitan. Non-limiting examples of Tween surfactants include Tween-20, Tween-40, Tween-60, and Tween-80.

By the term "anti-inflammatory agent" is meant any molecule that decreases (e.g., by at least 5%, 10%, 15%, 20%, 25%, 30%, 35%, 40%, 45%, 50%, 55%, 60%, 65%, 70%, 75%, 80%, 85%, 90%, or 95%) one or more symptoms of inflammation or one or more pain test scores in a subject (e.g., a human). Non-limiting examples of anti-inflammatory agents include a NSAIDs (e.g., COX-1 inhibitors and COX-2 inhibitors), DMARDs, steroids (e.g., corticosteroids), and TNF-α inhibitors. Specific examples of NSAIDs, DMARDs, COX-1 inhibitors, COX-2 inhibitors, steroids, and TNF-α inhibitors are described below. Natural anti-inflammatory agents include glucosamine, bromelin, rosemary oil, basil oil, turmeric oil, and ginger oil.

By the term "non-steroidal anti-inflammatory drug" or "NSAID" is meant a non-steroidal agent that diminishes inflammation. Non-limiting examples of NSAIDs include COX-1 inhibitors (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, tolmetin, etodolac, ketorolac, mefenamic acid, piroxicam, salsalate, and sulindac), and COX-2 inhibitors (e.g., rofecoxib, celecoxib, valdecoxib, lumiracoxib, and firocoxib).

By the term "disease-modifying anti-rheumatic drug" or "DMARD" is meant a therapeutic agent used for the treatment of an inflammatory disease. Non-limiting examples of DMARDs known in the art include: auranofin, aurothioglucose, azathioprine, chlorambucil, cyclophosphamide, D-penicillamine, gold sodium thiomalate (injectable gold), hydroxychloroquine, leflunomide, methotrexate, minocycline, mycophenolate mofetil, and sulfasalazine.

By the term "cyclooxygenase-1 inhibitor" or "COX-1 inhibitor" is meant a molecule that decreases the expression (e.g., mRNA or protein) or enzymatic activity of cycooxygenase-1. For example, a COX-1 inhibitor may decrease COX-1 expression levels (e.g., mRNA or protein) or enzymatic activity by at least 10% (e.g., at least 15%, 20%, 25%, 30%, 35%, 40%, 45%, 50%, 55%, 60%, 65%, 70%, 75%, 80%, 85%, 90%, or 95%). The expression level of COX-1 may be determined using immunoblotting, PCR (e.g., quantitative real-time PCR or gene array analysis), or Northern blot analysis. The enzymatic activity of COX-1 may be measured using biochemical assays known in the art. Non-limiting examples of COX-1 inhibitors include: naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, tolmetin, etodolac, ketorolac, mefenamic acid, piroxicam, salsalate, and sulindac.

By the term "cyclooxygenase-2 inhibitor" or "COX-2 inhibitor" is meant a molecule that decreases the expression (e.g., mRNA or protein) or enzymatic activity of cycooxygenase-2. For example, a COX-2 inhibitor may decrease COX-2 expression levels (e.g., mRNA or protein) or enzymatic activity by at least 10% (e.g., at least 15%, 20%, 25%, 30%, 35%, 40%, 45%, 50%, 55%, 60%, 65%, 70%, 75%, 80%, 85%, 90%, or 95%). The expression levels of COX-2 may be determined using immunoblotting, PCR (e.g., quantitative real-time PCR or gene array analysis), or Northern blot analysis. The enzymatic activity of COX-2 may be measured using biochemical assays known in the art. Non-limiting examples of COX-2 inhibitors include: rofecoxib, celecoxib, valdecoxib, lumiracoxib, and firocoxib.

By the term "tumor necrosis factor-α inhibitor" or "TNF-α inhibitor" is meant a molecule that binds and/or prevents (e.g., by at least 10%, 15%, 20%, 25%, 30%, 35%, 40%, 45%, 50%, 55%, 60%, 65%, 70%, 75%, 80%, 85%, 90%, or 95%) TNF-α from binding to a cognate receptor (a TNF-α receptor) or decreases (e.g., by at least 10%, 15%, 20%, 25%, 30%, 35%, 40%, 45%, 50%, 55%, 60%, 65%, 70%, 75%, 80%, 85%, 90%, or 95%) an activity (e.g., downstream intracellular signaling) of a TNF-α receptor. For example, a TNF-α inhibitor, such as a soluble fragment of a TNF-α receptor or an antibody, may bind TNF-α and prevent its ability to bind and/or activate a TNF-α receptor. Additional examples of TNF-α inhibitors may prevent the downstream activation of mitogen-activated protein kinase(s) (MAPKs) or nuclear factor kappa-light-chain-enhancer of activated B cells (NF-κB). Non-limiting examples of TNF-α inhibitors include: adalimumab, certolizumab, etanercept, golimumab, infliximab, thalidomide, lenalidomide, etanercept, pegsunercept, bupropion, and pentoxifylline.

By the term "steroid" is meant a molecule containing a sterane core composed of seventeen carbon atoms bonded together to form four fused rings: three cyclohexane rings and one cyclopentane ring. The steroids may have the ability to decrease (e.g., by at least 10%, 15%, 20%, 25%, 30%, 35%, 40%, 45%, 50%, 55%, 60%, 65%, 70%, 75%, 80%, 85%, 90%, or 95%) one or more symptoms of inflammation or one or more pain test scores in a subject. Non-limiting examples of steroids include: hydrocortisone, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, desamethasone, fluocortolone, hydrocortisone-17-butyrate, hydrocortisone-17-valerate, aclomestasone dipropionate, betamethasone valerate, betamethasone dipropionate, prednicarbate, clobetasone-17-buturate, clobetasol-17-propionate, fluocortolone caproate, fluocortolone pivalate, and fluprednidene acetate.

By the term "absorption enhancer" is meant any compound or combination of compounds that increases the absorption rate of an omega-3 oil (e.g., DHA and EPA) and/or one or more pharmaceutical agents (e.g., an anti-inflammatory agent, a gastrotoxic pharmaceutical agent, a nephrotoxic pharmaceutical agent, or a hepatotoxic pharmaceutical agent). Non-limiting examples of absorption enhancers include: ethanol, vitamin E, a polyethylene glycol, a Tween surfactant, cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides (MCTs), sodium lauryl sulfate, natural fish oil, palmitic monoglycerides or diglycerides, capric monoglycerides or diglycerides, amides of intermediate (C-8 to C-12) fatty acids (e.g., lauryl acid), and amides of long chain (C-13 to C-24) fatty acids (e.g., palmitic acid). In some implementations, the absorption enhancer includes at least one non-hydrophilic surfactant or co-solvent.

By the term "antihistamine" is meant any molecule that has H-1 receptor antagonism as defined by competition-based binding assays. In vitro and in vivo competition-based binding assays to measure H-1 receptor antagonism are known in the art. An antihistamine may be a member of the class of tricyclic antihistamines (e.g., doxepin and impramine) or a member of the class of non-tricyclic antihistamines (e.g., diphenhydramine and triprolidine).

By the term "hepatotoxicity" or "liver toxicity" is meant liver tissue damage or inflammation (e.g., damage or inflammation induced by a chemical, such as a prescribed medication). For example, hepatotoxicity may be induced by a pharmaceutical agent administered at a recommended dose over time (e.g., a NSAID). Non-limiting examples of symptoms of hepatotoxicity include: increased (e.g., by at least 10%, 15%, 20%, 25%, 30%, 35%, 40%, 45%, 50%, 55%, 60%, 65%, 70%, 75%, 80%, 85%, 90%, or 95%) aspartate aminotransferase levels in the blood; increased (e.g., by at least 10%, 15%, 20%, 25%, 30%, 35%, 40%, 45%, 50%, 55%, 60%, 65%, 70%, 75%, 80%, 85%, 90%, or 95%) alkaline phosphatase levels in the blood; increased (e.g., by at least 10%, 15%, 20%, 25%, 30%, 35%, 40%, 45%, 50%, 55%, 60%, 65%, 70%, 75%, 80%, 85%, 90%, or 95%) alanine transaminase levels in the blood, increased (e.g., by at least 10%, 15%, 20%, 25%, 30%, 35%, 40%, 45%, 50%, 55%, 60%, 65%, 70%, 75%, 80%, 85%, 90%, or 95%) total bilirubin in the blood, increased (e.g., by at least 10%, 15%, 20%, 25%, 30%, 35%, 40%, 45%, 50%, 55%, 60%, 65%, 70%, 75%, 80%, 85%, 90%, or 95%) gamma-glutamyltransferase levels in the blood, jaundice, abdominal pain or swelling, bloody stool, chronic fatigue, nausea, loss of appetite, and hepatomegaly. A subject experiencing hepatotoxicity may have at least a two-fold (e.g., at least three-fold, four-fold, or five-fold) increase in alanine transferase levels in the blood, at least a two-fold (e.g., at least three-fold, four-fold, or five-fold) increase in alkaline phosphatase levels in the blood, or at least a two-fold increase (e.g., at least three-fold, four-fold, or five-fold) in total bilirubin level in the blood compared a control subject or patient population.

By the term "nephrotoxicity" or "kidney toxicity" is meant kidney tissue damage or inflammation (e.g., damage or inflammation induced by a chemical, such as a prescribed medication). For example, nephrotoxicity may be induced by a pharmaceutical agent administered at a recommended dose over time (e.g., a NSAID). Non-limiting examples of symptoms of nephrotoxicity include: increased (e.g., by at least 10%, 15%, 20%, 25%, 30%, 35%, 40%, 45%, 50%, 55%, 60%, 65%, 70%, 75%, 80%, 85%, 90%, or 95%) urea nitrogen in the blood, increased (e.g., by at least 10%, 15%, 20%, 25%, 30%, 35%, 40%, 45%, 50%, 55%, 60%, 65%, 70%, 75%, 80%, 85%, 90%, or 95%) creatine levels in urine, increased (e.g., by at least 10%, 15%, 20%, 25%, 30%, 35%, 40%, 45%, 50%, 55%, 60%, 65%, 70%, 75%, 80%, 85%, 90%, or 95%) microalbumin in urine, nausea, vomiting, loss of appetite, and weakness (compared to a control subject or patient population).

By the term "gastrotoxicity" or "gastric toxicity" is meant damage or inflammation of stomach tissue (e.g., the lining of the stomach). For example, gastrotoxicity may be induced by a pharmaceutical agent administered at a recommended dose over time (e.g., a NSAID). Non-limiting examples of symptoms of gastrotoxicity include: nausea, vomiting, loss of appetite, bloating, belching, ulcers, stomach pains, occult blood in feces, and weight loss (compared to a control subject or patient population).

By the term "gastrotoxic, nephrotoxic, or hepatotoxic pharmaceutical agent" is meant a pharmaceutical agent (e.g., a prescribed medication) that induces gastrotoxicity, nephrotoxicity, or hepatotoxicity when administered to a subject (e.g., a human). For example, a gastrotoxic, nephrotoxic, or hepatotoxic pharmaceutical agent may be a pharmaceutical agent (e.g., a NSAID) administered at a prescribed dose over a prolonged period of time (e.g., at least 1 day, one week, two weeks, three weeks, one month, two months, three months, four months, five months, six months, seven months, eight months, nine months, ten months, eleven months, one year, two years, three years, four years, and five years). Non-limiting examples of gastrotoxic, nephrotoxic, and hepatotoxic pharmaceutical agents include: acetaminophen, ibuprofen, alpha-methyldopa, amiodarone, carbamazepine, chlorzoxazone, dantrolene, diclofenac, fluconazole, ketoconazole, flutamide, hydralazine, ibuprofen, imuran, azathioprine, isoniazid, ketek, long-acting nicotinic acid, zafirlukast accolade, zileuton, methotrexate, nitrofurantoin, perihexilene maleate, phenylbutazone, phenytoin, pravastin, fluvastatin, simavastatin, lovastatin, quinidine, rifampin, septra, bactrim, tacrine, tasmar, ticlid, troglitzone, clofarabine, pemetrexed, aldesleukin, fenofibrate, gemfibrozil, clofibrate, fenofibric acid, indomethacin, methotrexate sodium, ibuprofen, naproxen sodium, meloxicam, stavudine, didanosine, zidovudine, nevirapine, ritonavir, cisplatin, carboplatin, carmustine, mitomycin, amphotericin B, gentamycin, vancomycin, angiotensin-converting enzyme (ACE) inhibitors, furosemide, LDL/HDL- or triglyceride-modifying drug (e.g., a statin, fibrate, niacin, or niacin derivative), and an antihistamine.

By the term "HDL/LDL- or triglyceride-modifying drug" is meant a composition that mediates at least 10% (e.g., at least 15%, 20%, 25%, 30%, 35%, 40%, 45%, 50%, 55%, 60%, 65%, or 70%) decrease in total high density lipoprotein (HDL) cholesterol levels in a subject, at least a 10% (e.g., at least 15%, 20%, 25%, 30%, 35%, 40%, 45%, 50%, 55%, 60%, 65%, or 70%) increase in total low density lipoprotein (LDL) cholesterol levels in a subject, and/or at least a 10% (e.g., at least 15%, 20%, 25%, 30%, 35%, 40%, 45%, 50%, 55%, 60%, 65%, or 70%) decrease in total triglyceride levels in a subject. Non-limiting examples of an HDL/LDL- or triglyceride-modifying drug include statins, fibrates, niacin, and niacin derivatives. Several additional HDL/LDL- or triglyceride-modifying drugs are presently known in the art.

By the term "reducing a symptom of gastrotoxicity, nephrotoxicity, or hepatotoxicity" is meant a reduction by at least 10% (e.g., by at least 10%, 15%, 20%, 25%, 30%, 35%, 40%, 45%, 50%, 55%, 60%, 65%, 70%, 75%, 80%, 85%, 90%, or 95%) in at least one (e.g., at least two, three, four, or five) symptoms of gastrotoxicity, nephrotoxicity, or hepatotoxicity. Non-limiting examples of such a reduction include: a decrease (e.g., by at least 10%, 15%, 20%, 25%, 30%, 35%, 40%, 45%, 50%, 55%, 60%, 65%, or 70%) in aspartate aminotransferase levels in the blood; a decrease (e.g., by at least 10%, 15%, 20%, 25%, 30%, 35%, 40%, 45%, 50%, 55%, 60%, 65%, or 70%) in alkaline phosphatase levels in the blood; a decrease (e.g., by at least 10%, 15%, 20%, 25%, 30%, 35%, 40%, 45%, 50%, 55%, 60%, 65%, or 70%) in alanine transaminase levels in the blood, a decrease (e.g., by at least 10%, 15%, 20%, 25%, 30%, 35%, 40%, 45%, 50%, 55%, 60%, 65%, or 70%) in total bilirubin levels in the blood, a decrease (e.g., by at least 10%, 15%, 20%, 25%, 30%, 35%, 40%, 45%, 50%, 55%, 60%, 65%, or 70%) in gamma-glutamyltransferase levels in the blood, a decrease (e.g., by at least 10%, 15%, 20%, 25%, 30%, 35%, 40%, 45%, 50%, 55%, 60%, 65%, or 70%) in urea nitrogen in the blood, a decrease (e.g., by at least 10%, 15%, 20%, 25%, 30%, 35%, 40%, 45%, 50%, 55%, 60%, 65%, or 70%) in creatine levels in urine, a decrease (e.g., by at least 10%, 15%, 20%, 25%, 30%, 35%, 40%, 45%, 50%, 55%, 60%, 65%, or 70%) in microalbumin in urine, decreased jaundice, a reduction in abdominal pain or swelling, a reduction in bloody stool, reduced fatigue, reduced nausea or vomiting (e.g., frequency or periodicity), a decrease in loss of appetite, decreased bloating, decreased belching, decreased ulcers, decreased stomach pain, reduced occult blood in feces, and reduced hepatomegaly.

By the phrase "decreasing the likelihood of developing" is meant a reduction (e.g., at least 5%, 10%, 15%, 20%, 25%, 30%, 35%, 40%, 50%, 60%, 70%, 80%, 90%, or 95%) for a subject or a patient population in the chance or rate of developing a specific disease (e.g., gastrotoxicity, nephrotoxicity, or hepatotoxicity) by administering one or more pharmaceutical compositions compared to a subject or patient population not receiving the one or more pharmaceutical compositions. The methods of the invention may also reduce the likelihood of developing one or more (e.g., one, two, three, four, or five) symptoms of a disease (e.g., gastrotoxicity, nephrotoxicity, or hepatotoxicity) in a patient population or a subject receiving one or more of the provided pharmaceutical compositions.

By "treating" a disease in a subject is meant reducing the severity or duration of at least one symptom (e.g., one, two, three, four, or five symptoms) of the disease by administrating one or more pharmaceutical composition(s) to the subject.

By the term "decreasing pain in a subject" is meant a decrease (e.g., at least 5%, 10%, 15%, 20%, 25%, 30%, 35%, 40%, 45%, 50%, 55%, 60%, 65%, 70%, 75%, 80%, 85%, 90%, or 95%) in the pain test score of a subject or patient population receiving therapeutic treatment compared to the pain test score of a subject or patient population prior to treatment or the pain test score of a subject or patient population not receiving the therapeutic treatment. Non-limiting examples of tests to quantify pain in a subject include: Alder Hey Triage Pain Score, Brief Pain Inventory (BPI), Dallas Pain Questionnaire, Dolorimeter Pain Index (DPI), Faces Pain Scale-Revised (FPS-R), Face Legs Arms Cry Consolability scale, McGill Pain Questionnaire (MPQ), Descriptor Differential Scale (DDS), Neck Pain and Disability Scale (NPAD), Numerical 11 point box (BS-11), Numeric Rating Scale (NRS-11), Roland-Morris Back Pain Questionnaire, Wong-Baker FACES Pain Rating Scale, Visual Analog Scale (VAS), and Disease Activity Score (DAS). A decrease in pain may result in at least a 5% decrease (e.g., at least a 10%, 15%, 20%, 25%, 30%, 35%, 40%, 45%, 50%, 55%, 60%, 65%, 70%, 75%, 80%, 85%, 90%, or 95% decrease) in one or more (e.g., one, two, three, or four) of the pain test scores listed above.

By the term "decreasing inflammation in a subject" or "decreasing at least one symptom of inflammation" is meant a decrease (e.g., at least 5%, 10%, 15%, 20%, 25%, 30%, 35%, 40%, 45%, 50%, 55%, 60%, 65%, 70%, 75%, 80%, 85%, 90%, or 95% decrease) in the severity or duration of one or more symptoms (e.g., one, two, three, four, or five symptoms) of inflammation in a subject receiving treatment compared to the severity or duration of one or more symptoms of inflammation in the subject prior to treatment or the severity or duration of one or more symptoms of inflammation in a subject or patient population not receiving therapeutic treatment. Non-limiting examples of symptoms of inflammation include: increased (e.g., by at least 5%, 10%, 15%, 20%, 25%, 30%, 35%, 40%, 45%, 50%, 55%, 60%, 65%, 70%, 75%, 80%, 85%, 90%, or 95%) COX-1 and/or COX-2 activity, increased (e.g., by at least 5%, 10%, 15%, 20%, 25%, 30%, 35%, 40%, 45%, 50%, 55%, 60%, 65%, 70%, 75%, 80%, 85%, 90%, or 95%) white blood cell count, increased (e.g., by at least 5%, 10%, 15%, 20%, 25%, 30%, 35%, 40%, 45%, 50%, 55%, 60%, 65%, 70%, 75%, 80%, 85%, 90%, or 95%) C-reactive protein, interleukin-6, and/or TNF-α levels, swelling, pain, and increased (e.g., by at least 5%, 10%, 15%, 20%, 25%, 30%, 35%, 40%, 45%, 50%, 55%, 60%, 65%, 70%, 75%, 80%, 85%, 90%, or 95%) erythrocyte sedimentation rate. The methods of the invention may result in a reduction (e.g., by at least 5%, 10%, 15%, 20%, 25%, 30%, 35%, 40%, 45%, 50%, 55%, 60%, 65%, 70%, 75%, 80%, 85%, 90%, or 95%) in COX-1 and/or COX-2 activity, a decrease (e.g., by at least 5%, 10%, 15%, 20%, 25%, 30%, 35%, 40%, 45%, 50%, 55%, 60%, 65%, or 70%) in the white blood cell count, a decrease (e.g., by at least 5%, 10%, 15%, 20%, 25%, 30%, 35%, 40%, 45%, 50%, 55%, 60%, 65%, 70%, 75%, 80%, 85%, 90%, or 95%) in C-reactive protein, interleukin-6, and/or TNF-alpha levels, decreased swelling, decreased pain (e.g, at least a 5%, 10%, 15%, 20%, 25%, 30%, 35%, 40%, 45%, 50%, 55%, 60%, 70%, 80%, 90%, or 95% decrease in one or more (e.g., one, two, three, four, or five) of the pain scores listed above), and a decrease (e.g., by at least 5%, 10%, 15%, 20%, 25%, 30%, 35%, 40%, 45%, 50%, 55%, 60%, or 70%) in erythrocyte sedimentation rate.

By the term "synergistic" is meant an effect observed using a combination of two or more agents that is greater than the sum of the effects of two or more agents when used or administered alone.

By the term "syngergistic decrease" is meant a decrease (e.g., in severity or duration) in one or more (e.g., at least two, three, four, or five) symptoms of a disease observed using a combination of two or more agents (e.g., pharmaceutical agents) that is greater than the decrease in one or more symptoms expected from the sum of the effects observed using the two or more agents alone.

By the term "liquid formulation" is meant the dissolving of a solid organic compound in an omega-3 fatty acid-based oil or the suspension of an organic compound in an omega-3 oil-based formulation. Thus, liquid formulation may also contain other absorption enhancers (surfactants) that increase the absorption efficiency, decrease the variability of absorption, improve C max, or favorably alter the AUC or t ½.

By the term "increased risk of having a stroke" is meant a subject or patient population that has been identified as having at least a 10% (e.g., at least 15%, 20%, 25%, 30%, 35%, 40%, 45%, 50%, 55%, 60%, 65%, 70%, 75%, 80%, 85%, 90%, 95%, or 100%) increase in the likelihood of having a stroke. The likelihood of having a stroke may be determined by reviewing the medical history of a subject, including family history of disease and subject's behavior and diet.

The recitation herein of numerical ranges by endpoints is intended to include all numbers subsumed within that range (e.g., a recitation of 1 to 5 includes 1, 1.5, 2, 2.75, 3, 3.80, 4, and 5).

As used herein, "a" or "an" means "at least one" or "one or more" unless otherwise indicated. In addition, the singular forms "a", "an" and "the" include plural referents unless the context clearly dictates otherwise. Thus, for example, reference to a composition containing "a compound" includes a mixture of two or more compounds.

Other features and advantages of the invention will be apparent from the following description of the preferred embodiments thereof, and from the claims.

DETAILED DESCRIPTION

We have discovered a new method for decreasing inflammation, pain, gastrotoxicity, nephrotoxcity, and hepatotoxicity by using compositions containing omega-3 oils. The invention therefore features compositions containing omega-3 oils, including formulations with increased absorption rates, for decreasing inflammation, pain, gastrotoxicity, nephrotoxcity, and hepatotoxicity in a subject (e.g., a human), kits containing these compositions, and methods for decreasing inflammation, pain, gastrotoxicity, nephrotoxicity, hepatotoxicity, and one or more symptoms of an allergic condition in a subject (e.g., a human) or a companion animal (e.g., a dog, cat, bird, and horse). The invention further provides methods for concentrating omega-3 oils (e.g., for use in the preparation of such pharmaceutical compositions) and methods for formulating anti-inflammatory agents.

Pharmaceutical Compositions

The invention provides pharmaceutical compositions containing omega-3 oils and at least one (e.g., at least two, three, four, or five) anti-inflammatory agent and/or at least one (e.g., at least two, three, four, or five) gastrotoxic, nephrotoxic, or hepatotoxic pharmaceutical agent. In one example, the anti-inflammatory agent (e.g., a NSAID) may also be gastrotoxic, nephrotoxic, or hepatotoxic. Desirably, the compositions are formulated as a liquid for oral administration.

The omega-3 oils included in the pharmaceutical compositions may be obtained from a natural source, including, for example, cold water oily fish (e.g., salmon, tuna, herring, mackerel, anchovies, and sardines), pollock, cod, catfish, flounder, grouper, halibut, mahi mahi, orange roughy, red snapper, shark, swordfish, tilefish, plankton, algae, krill, green-lipped mussel, chia seeds, kiwifruit seeds, perilla seeds, flax seeds, lingonberry seeds, camelina seeds, purslane seeds, black raspberry seeds, hemp seeds, butternut, walnuts, pecan nuts, and hazel nuts. The omega-3 oil included in the pharmaceutical compositions may be high grade (e.g., at least 70%, 75%, 80%, 85%, 90%, 91%, 92%, 93%, 94%, 95%, 96%, 97%, 98%, or 99% pure).

In one example, the high grade omega-3 oil used in the pharmaceutical compositions is OmegaMaine omega-3 oils. A unit dose containing 10 mL of OmegaMaine omega-3 oil contains 1,625 mg to 1,900 mg of EPA and 1,525 mg to 1,700 mg of DHA. The total active dose of EPA and DHA in 10 mL of OmegaMaine omega-3 oil is in the range of 3,150 mg to 3,600 mg of omega-3 oil. The total monsaturated fats in of OmegaMaine omega-3 oil by weight is in the range of 25% to 31%, and the total saturated fats is in the range of 23% to 25%. The ratio of EPA to DHA in OmegaMaine omega-3 oil may range between 40:60 to 60:40 (e.g., 50:50).

In other examples of the pharmaceutical compositions, the omega-3 oil is an alkyl ester of a fatty acid (e.g., an alkyl ester of EPA or DHA), or a mixture of EPA and DHA. In other embodiments, the omega-3 oils present in the compositions are in the form of triglycerides or a mixture of triglycerides and free fatty acids.

In additional non-limiting examples of the pharmaceutical compositions, the omega-3 oil is at least 25% (e.g., at least 30%, 35%, 40%, 45%, 50%, 55%, 65%, 70%, 75%, 80%, 85%, 90%, or 95%) of the composition's total mass or at least 50% of the composition's total volume (e.g., at least 55%, 60%, 65%, 70%, 75%, 80%, 85%, 90%, or 95%) (e.g., a liquid composition). In one implementation of the invention, at least 10% (e.g., at least 15%, 20%, 25%, 30%, 35%, 40%, 45%, or 50%) of the omega-3 oil in the composition is in solution and at least 50% (e.g., at least 55%, 60%, 65%, 70%, 75%, 80%, 85%, 90%, or 95%) of the omega-3 oil in the composition is in stable suspension form. The omega-3 oil is typically a mixture of one or more omega-3 fatty acids, including EPA, DHA, or a combination thereof. The Omega-3 oil composition may include, for example, an omega-3 oil composition as is described in U.S. Provisional Application No. 61/383,972, entitled "Compositions Containing Omega-3 Oils and Uses Thereof," filed on even date herewith, which is incorporated herein in its entirety by reference.

The anti-inflammatory agent(s) included in the compositions of the invention may be synthetically generated or purified from a natural source (e.g., natural anti-inflammatory agent), may have a molecular weight between 100 g/mole and 800 g/mole (e.g., between 100 g/mole and 400 g/mole, between 400 g/mole and 800 g/mole, between 200 g/mole and 700 g/mole, and between 300 g/mole and 600 g/mole), a log P value greater than 2 (e.g., greater than 2.5, greater than 3.0, greater than 3.5, and greater than 4.0), and/or a melting point of below 200° C. (e.g., below 180° C., below 160° C., and below 140° C.). Non-limiting examples of natural anti-inflammatory agents include: glucosamine, bromelin, rosemary oil, basil oil, turmeric oil, and ginger oil. Additional examples of anti-inflammatory agents include NSAIDs (e.g., COX-1 inhibitors and COX-2 inhibitors), DMARDs, steroids, and TNF-α inhibitors. Non-limiting examples of COX-1 inhibitors that may be included in the provided compositions are: naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, tolmetin, etodolac, ketorolac, mefenamic acid, piroxicam, salsalate, and sulindac. Non-limiting examples of COX-2 inhibitors that may be included in the compositions are: rofecoxib, celecoxib, valdecoxib, lumiracoxib, and firocoxib. Non-limiting examples of DMARDs that may be included in the compositions are: auranofin, aurothioglucose, azathioprine, chlorambucil, cyclophosphamide, D-penicillamine, gold sodium thiomalate (injectable gold), hydroxychloroquine, leflunomide, methotrexate, minocycline, mycophenolate mofetil, and sulfasalazine. Non-limiting examples of steroids that may be included in the provided compositions are: hydrocortisone, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, desamethasone, fluocortolone, hydrocortisone-17-butyrate, hydrocortisone-17-valerate, aclomestasone dipropionate, betamethasone valerate, betamethasone dipropionate, prednicarbate, clobetasone-17-buturate, clobetasol-17-propionate, fluocortolone caproate, fluocortolone pivalate, and fluprednidene acetate. Non-limiting examples of TNF-α inhibitors that may be included in the compositions are: adalimumab, certolizumab, etanercept, golimumab, infliximab, thalidomide, lenalidomide, etanercept, pegsunercept, bupropion, and pentoxifylline. The compositions provided by the invention may include any combination of two or more (e.g., two, three, or four) of the above classes of anti-inflammatory agents, for example, a COX-1 inhibitor and a COX-2 inhibitor; a COX-1 inhibitor, a COX-2 inhibitor, and a DMARD; a COX-1 inhibitor, a COX-2 inhibitor, and a steroid; a COX-1 inhibitor, a COX-2 inhibitor, a DMARD, and a steroid; a COX-1 inhibitor, a COX-2 inhibitor, a steroid, and a TNF-α inhibitor; and a steroid and a TNF-α inhibitor. The amount of one or more anti-inflammatory agents present in a single dose of the provided compositions may be at least 0.1% of the composition's total mass (e.g., at least 1%, at least 2%, at least 3%, at least 4%, at least 5%, at least 10%, at least 15%, at least 20%, at least 25%, at least 30%, at least 35%, or at least 40% of the composition's total mass, or between 0.1% and 20%, between 0.1% and 10%, between 10% and 20%, or between 5% and 15% of the composition's total mass). In specific examples, the anti-inflammatory agent is dissolved in a solution containing ethanol. In desirable embodiments, both the omega-3 oil and the anti-inflammatory agent(s) are present in amounts sufficient to result in a therapeutic effect (e.g., a decrease in one or more symptoms of inflammation or a decrease in one or more pain test scores in a subject or patient population compared to a subject or patient population prior to treatment or a subject or patient population not receiving treatment). In other embodiments, the omega-3 oil is an active component in the pharmaceutical dosage form and represents at least 50% (e.g., at least 60%, 70%, 80%, or 90% of the composition's total weight). In another example, the omega-3 oil and the anti-inflammatory agent(s) are present in amounts sufficient to result in a decrease in the amount of coumadin and/or warfarin administered to a subject having an increased risk of having a stroke (e.g., at least a 10%, 20%, 30%, 40%, 50%, 60%, 70%, 80%, 90%, or 100% risk of having a stroke).

The gastrotoxic, nephrotoxic, or hepatotoxic pharmaceutical agents that may be included in the compositions of the invention may include any known synthetic or natural agent that is known to induce gastrotoxicity, nephrotoxicity, or hepatotoxicity in a subject following administration to a subject (e.g., following at administration for at least one day, one week, two weeks, three weeks, one month, two months, three months, four months, five months, six months, seven months, eight months, nine months, ten months, eleven months, one year, two years, three years, four years, and five years) and may have a molecular weight between 100 g/mole and 800 g/mole (e.g., between 100 g/mole and 400 g/mole, between 400 g/mole and 800 g/mole, between 200 g/mole and 700 g/mole, and between 300 g/mole and 600 g/mole), a log P value greater than 2 (e.g., greater than 2.5, greater than 3.0, greater than 3.5, and greater than 4.0), and/or a melting point of below 200° C. (e.g., below 180° C., below 160° C., and below 140° C.). These gastrotoxic, nephrotoxic, or hepatotoxic pharmaceutical agents may administered to decrease one or more symptoms (e.g., pain and inflammation) of any disease state (e.g., cancer, viral infection (e.g., HIV), arthritis (e.g., rheumatoid arthritis and osteoarthritis), Crohn's disease, liver disease, inflammatory heart disease, kidney disease, gastritis, gingivitis, periodontal disease, asthma, chronic obstructive pulmonary disease, autoimmune diseases, irritable bowel syndrome, fibromyalgesia, leg pains, restless leg syndrome, neuropathic pain, and diabetic neuropathy). Non-limiting examples of gastrotoxic, nephrotoxic, or hepatotoxic pharmaceutical agents that may be included in the compositions of the invention include: acetaminophen, ibuprofen, alpha-methyldopa, amiodarone, carbamazepine, chlorzoxazone, dantrolene, diclofenac, fluconazole, ketoconazole, flutamide, hydralazine, ibuprofen, imuran, azathioprine, isoniazid, ketek, long-acting nicotinic acid, zafirlukast accolade, zileuton, methotrexate, nitrofurantoin, perihexilene maleate, phenylbutazone, phenytoin, pravastin, fluvastatin, simavastatin, lovastatin, quinidine, rifampin, septra, bactrim, tacrine, tasmar, ticlid, troglitzone, clofarabine, pemetrexed, aldesleukin, fenofibrate, gemfibrozil, clofibrate, fenofibric acid, indomethacin, methotrexate sodium, ibuprofen, naproxen sodium, meloxicam, stavudine, didanosine, zidovudine, nevirapine, ritonavir, cisplatin, carboplatin, carmustine, mitomycin, amphotericin B, gentamycin, vancomycin, angiotensin-converting enzyme (ACE) inhibitors, furosemide, an antihistamine, and HDL/LDL- or triglyceride-modifying agents (e.g., statins, niacin, niacin derivatives, and fibrates (e.g., fibric acid or fenofibrate).

In addition to the omega-3 oil and the anti-inflammatory agent(s) or gastrotoxic, nephrotoxic, or hepatotoxic pharmaceutical agent(s), the compositions of the invention may also include one or more (e.g., at least two, three, four, five, six, seven, eight, nine, or ten) absorption enhancers in order to increase the rate of absorption. Absorption enhancers included in the compositions may be any solvent or agent that enhances the absorption rate of omega-3 oils, anti-inflammatory agents, and/or gastrotoxic, nephrotoxic, or hepatotoxic pharmaceutical agents in a subject (e.g., a human or an animal, in particular a companion animal, such as a dog or a cat). Non-limiting examples of absorption enhancers that may be included in the compositions are: ethanol, vitamin E, a polyethylene glycol, a Tween surfactant (e.g., Tween-80, Tween-60, Tween-40, and Tween-20), cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides (MCTs), sodium lauryl sulfate, natural fish oil, palmitic monoglycerides or diglycerides, capric monoglycerides or diglycerides, amides of intermediate (C-8 to C-12) fatty acids (e.g., lauryl acid), and amides of long chain (C-13 to C-24) fatty acids (e.g., palmitic acid). The amides of fatty acids may be derived from naturally-occurring amino acids (e.g., glycine, lysine, and alanine). In examples of the provided pharmaceutical compositions, the one or more absorption enhancer(s) are less than 30% (e.g., less than 25%, 20%, 15%, 10%, or 5%) of the composition's total mass.

Non-limiting examples of the provided compositions contain vitamin E as an absorption enhancer and rosemary oil as a natural anti-inflammatory agent. In additional examples of the compositions, one or more of natural fish oil, palmitic monoglycerides or diglycerides, or capric monoglycerides or diglycerides are included as absorption enhancers. In other examples of the provided compositions, the absorption enhancers present in the composition (e.g., between 1% and 10% of the composition's total mass) include one or more of: phosphatidylinositol, phosphatidylserine, phosphatidylcholine, phosphatidylethanolamine, and phosphatadic acid (e.g., phosphatidylcholine, phosphatidylserine, and phosphatidic acid). Additional examples of the composition contain 1% to 5% of polytocopherol, 1% to 5% arginine or citrulline, and/or 1% to 10% medium chain triglycerides (e.g., coconut oil) as absorption enhancer(s).

Examples of the provided pharmaceutical compositions contain (by weight): 60% to 80% of omega-3 oil; 0.5% to 5% rosemary oil; 1% to 10% mixture of phosphatidylserine, phosphatidylcholine, and phosphatidic acid; 1% to 5% polytocopherol; 1% to 5% arginine or citrulline; and 1% to 10% medium chain triglycerides.

Additional examples of the provided pharmaceutical compositions contain (by weight): 60% to 80% omega-3 oil; 0.5% to 5% rosemary oil; 1% to 10% mixture of phosphatidylserine, phosphatidylcholine, and phosphatidic acid; 1% to 5% polytocopherol; and 1% to 5% arginine or citrulline; and 1% to 20% anti-inflammatory agent(s) (e.g., NSAID(s), DMARDs, steroids, and TNF-α inhibitors) and/or gastrotoxic, nephrotoxic, or hepatotoxic pharmaceutical agent(s). A specific final clinical formulation will vary depending on the physical chemistry of the pharmaceutical agent. For example, the ethanol concentration may be reduced to 1% to 5% and the other ingredients increased.

A single dose of the provided pharmaceutical compositions may contain greater than 2.5 g (e.g., greater than 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, or 5.0 g) combined of EPA and DHA. For example, a single dose of the pharmaceutical composition may contain greater than 2.5 g (e.g., greater than 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, or 5.0 g) combined of EPA and DHA in a volume of at least 5.0 mL (e.g., at least 5.5 mL, 6.0 mL, 6.5 mL, 7.0 mL, 7.5 mL, 8.0 mL, 8.5 mL, 9.0 mL, 9.5 mL, 10.0 mL, 10.5 mL, 11.0 mL, 11.5 mL, 12.0 mL, 12.5 mL, 13.0 mL, 13.5 mL, 14.0 mL, 14.5 mL, or 15.0 mL).

A single dose of the provided pharmaceutical composition may contain between 0.1 mg and 2.0 g (e.g., between 0.1 mg and 1.5 mg, 0.1 mg and 1 g, 0.1 mg and 750 mg, 1 mg and 650 mg, 1 mg and 550 mg, 1 mg and 500 mg, 10 mg and 450 mg, 10 mg and 400 mg, 10 mg and 350 mg, 10 mg and 350 mg, and 10 mg and 250 mg) of each of the one or more (e.g., at least two, three, four, or five) anti-inflammatory agents (e.g., a NSAID, DMARD, steroid, and TNF-α inhibitor) or each of the one or more (e.g., at least two, three, four, or five) gastrotoxic, nephrotoxic, or hepatotoxic pharmaceutical agent(s).

The compositions may be formulated using any known method, including oral formulations such as a pill (e.g., bilayered or trilayered pill), a fluid, a capsule, or a dietary supplement (e.g., a shake or bar). The compositions may also be formulated for intramuscular, intraocular, intranasal, subcutaneous, intraarterial, and intravenous administration.

Kits

The invention further provides kits containing one or more (e.g., at least 2, 3, 4, 5, 6, 7, 8, 9, or 10) of the pharmaceutical compositions described herein. Desirably, the pharmaceutical compositions included in the kits are formulated for oral administration. The kits may further contain materials to aid in the administration of the pharmaceutical compositions (e.g., a syringe). Desirably, the kits provide compositions in one or more oral liquid formulation(s). The liquid formulation will desirably demonstrate improved absorption kinetics (e.g., reduced variability in absorbance and increased rate of absorption relative to solid oral compositions) and offer for ease of dosing in patients that have difficulty swallowing (dysphagia). The kits may contain one or more doses of a pharmaceutical compositions provided by the invention. The kits may further contain instructions for administering the pharmaceutical compositions to a subject having inflammation (e.g., inflammation associated with a specific disease state, e.g., those diseases described herein), pain (e.g., pain associated with a specific disease state, chronic pain, neuropathic pain, or acute pain), gastrotoxicity (e.g., drug-induced gastrotoxicity), nephrotoxicity (e.g., drug-induced nephrotoxicity), or hepatotoxicity (e.g., drug-induced hepatotoxicity).

The kits may also include one or more (e.g., at least two, three, or four) additional compositions containing an anti-inflammatory agent (e.g., a NSAID (e.g., COX-1 and COX-2 inhibitor), a DMARD, a steroid, or a TNF-α inhibitor) or one or more (e.g., at least two, three, or four) additional gastrotoxic, nephrotoxic, or hepatotoxic pharmaceutical agents. The instructions provided with the kits may indicate that the one or more additional compositions containing an anti-inflammatory agent and/or a gastrotoxic, nephrotoxic, or hepatotoxic pharmaceutical agent be administered to the subject at the same time (co-administered) as the pharmaceutical compositions containing omega-3 oils (described above) or may indicate that the one or more additional compositions containing an anti-inflammatory agent and/or a gastrotoxic, nephrotoxic, or hepatotoxic pharmaceutical agent be delivered after administration (e.g., within 1 minute, 5 minutes, 10 minutes, 15 minutes, 20 minutes, 30 minutes, 45 minutes, 1 hour, 2 hours, 3 hours, 4 hours, 5 hours, 6 hours, 7 hours, 8 hours, 9 hours, 10 hours, or 12 hours) of the pharmaceutical compositions containing omega-3 oils described herein.

Methods of Formulating Anti-Inflammatory Agents

The invention further provides methods of formulating an omega-3 oil composition containing at least one (e.g., at least two, three, four, or five) anti-inflammatory agent (e.g., a NSAID, DMARD, steroid, and TNF-α inhibitor) and/or at least one (e.g., at least two, three, four, or five) gastrotoxic, nephrotoxic, or hepatotoxic pharmaceutical agent in order to increase absorption rate (relative to absorption rate of omega-3 oil alone, the anti-inflammatory agent alone, or the gastrotoxic, nephrotoxic, or hepatotoxic pharmaceutical agent alone). These methods require the step of combining an omega-3 oil (e.g., purified or in a natural form (e.g., natural fish oil)) and anti-inflammatory agent(s) and/or gastrotoxic, nephrotoxic, or hepatotoxic agent(s) with one or more (e.g., at least two, three, four, five, six, seven, eight, nine, or ten) absorption enhancers. Non-limiting absorption enhancers that may be used to formulate the compositions include: ethanol, vitamin E, a polyethylene glycol, a Tween surfactant (e.g., Tween-80, Tween-60, Tween-40, and Tween-20), cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides (MCTs), natural fish oil, palmitic monoglycerides or diglycerides, capric monoglycerides or diglycerides, amides of intermediate (C-8 to C-12) fatty acids (e.g., lauryl acid), and amides of long chain (C-13 to C-24) fatty acids (e.g., palmitic acid). The amides of fatty acids may be derived from naturally-occuring amino acids such as alanine, lysine, or glycine.

In additional examples of these methods, the one or more anti-inflammatory molecules(s) and/or one or more gastrotoxic, nephrotoxic, or hepatotoxic pharmaceutical agent(s) are first combined with one or more absorption enhancers (e.g., ethanol, a Tween surfactant (e.g., Tween-80, Tween-60, Tween-40, and Tween-20), MCTs, vitamin E, and lecithin)) to solubilize the one or more anti-inflammatory agent(s) (e.g., NSAID) and/or one or more gastrotoxic, nephrotoxic, or hepatotoxic pharmaceutical agents, and then the omega-3 oil is added to form the pharmaceutical composition.

Methods of Concentrating an Omega-3 Oil

The invention further provides methods of concentrating omega-3 oil requiring the steps of: decreasing the temperature of an omega-3 oil (e.g., an oil derived from natural source, such as salmon, herring, mackerel, and sardines) from 36° F. to 34° F. and incubating the oil at 34° F. for at least 1 hour (e.g., at least 2 hours, at least 3 hours, at least 4 hours, at least 5 hours, at least 6 hours, at least 12 hours, at least 24 hours, between 1 hour and 24 hours, between 1 hour and 12 hours, between 2 hours and 12 hours, between 3 hours and 12 hours, between 6 hours and 12 hours, between 5 hours and 10 hours, between 12 hours and 24 hours, between 14 hours and 20 hours, and between 16 hours and 20 hours), whereby the decrease in temperature results in the precipitation of high molecular weight lipids and fatty acids; recovering the liquid phase; decreasing the temperature of the recovered liquid from 36° F. to 34° F., and incubating the liquid at 34° F. for at least 1 hour (e.g., at least 2 hours, at least 3 hours, at least 4 hours, at least 5 hours, at least 6 hours, at least 12 hours, at least 24 hours, at least 36 hours, between 24 hours and 36 hours, between 1 hour and 36 hours, between 2 hours and 12 hours, between 6 hours and 24 hours, between 12 hours and 24 hours, and between 30 hours and 36 hours) whereby the 34° F. incubation results in the formation of a clarified liquid; and recovering the clarified liquid containing concentrated omega-3 oil (e.g., having a decreased density (e.g., at least 5%, 10%, 15%, 20%, 25%, or 30% decrease) compared to the starting omega-3 oil).

In non-limiting examples of these methods, the liquid phase or the clarified liquid may be removed by decantation. In additional examples of these methods, the recovery of the liquid phase or the clarified liquid may be aided or performed in part by centrifugation or filtration. These methods may yield an omega-3 oil that is concentrated by at least 10% (e.g., by at least 15%, at least 20%, at least 25%, at least 30%, at least 35%, at least 40%, at least 45%, at least 50%, at least 55%, at least 60%, or at least 70%). These methods may also yield an omega-3 that is at least 70% pure (e.g., at least 75%, 80%, 85%, 90%, or 95% pure).

Methods of Treating Pain, Inflammation, and an Allergic Condition

The invention also provides methods for decreasing pain (e.g., decreasing at least one (e.g., at least two, three, four, or five pain test scores) or decreasing at least one symptom (e.g., at least two, three, four, or five symptoms) of inflammation or an allergic condition in a subject comprising administering to the subject one or more (e.g., at least two, three, four, or five) of the pharmaceutical compositions described herein.

Pain may be monitored by a physician using one or more pain score tests to quantify pain in a subject. Non-limiting examples of such pain score tests include: Alder Hey Triage Pain Score, Brief Pain Inventory (BPI), Dallas Pain Questionnaire, Dolorimeter Pain Index (DPI), Faces Pain Scale-Revised (FPS-R), Face Legs Arms Cry Consolability scale, McGill Pain Questionnaire (MPQ), Descriptor Differential Scale (DDS), Neck Pain and Disability Scale (NPAD), Numerical 11 point box (BS-11), Numeric Rating Scale (NRS-11), Roland-Morris Back Pain Questionnaire, Wong-Baker FACES Pain Rating Scale, Visual Analog Scale (VAS), and Disease Activity Score (DAS). Likewise, a physician may monitor inflammation by measuring one or more of the following symptoms in a subject: increased (e.g., by at least 5%, 10%, 15%, 20%, 25%, 30%, 35%, 40%, 45%, 50%, 55%, 60%, 65%, 70%, 75%, 80%, 85%, 90%, or 95%) COX-1 and/or COX-2 activity, increased (e.g., by at least 5%, 10%, 15%, 20%, 25%, 30%, 35%, 40%, 45%, 50%, 55%, 60%, 65%, 70%, 75%, 80%, 85%, 90%, or 95%) white blood cell count, increased (e.g., by at least 5%, 10%, 15%, 20%, 25%, 30%, 35%, 40%, 45%, 50%, 55%, 60%, 65%, 70%, 75%, 80%, 85%, 90%, or 95%) C-reactive protein, interleukin-6, and/or TNF-alpha levels, swelling, pain, and increased (e.g., by at least 5%, 10%, 15%, 20%, 25%, 30%, 35%, 40%, 45%, 50%, 55%, 60%, 65%, 70%, 75%, 80%, 85%, 90%, or 95%) erythrocyte sedimentation rate. A physician may monitor an allergic condition by measuring one or more of the symptoms of an allergic condition (e.g., allergen-induced dermatitis, rhinitis, and seasonal allergies). Non-limiting examples of symptoms of an allergic condition include: nasal congestion, sneezing, runny nose, watery eyes, swollen eyes, itchy nose, itchy skin, itchy eyes, tingling mouth, swelling of the lips, mouth, or throat, hives, anaphylaxis, rash, and wheezing. In examples of the provided methods, a subject is administered a first composition containing an omega-3 oil and a second composition containing at least one (e.g., at least two, three, four, or five) anti-inflammatory agent (e.g., a natural anti-inflammatory agent (e.g., rosemary oil), a NSAID (e.g., COX-1 and COX-2 inhibitor), a DMARD, a steroid, an anti-histamine (e.g., a tricyclic antihistamine or a non-tricyclic antihistamine) and a TNF-α inhibitor), whereby the administration of these compositions results in a synergistic decrease in at least one (e.g., at least two, three, four, or five) symptom of inflammation or an allergic condition or a synergistic decrease in at least one (e.g., at least two, three, four, or five) pain test score(s) in the patient compared to the sum of the effect of the first composition alone and the effect of the second composition alone on the symptom(s) of inflammation or the test pain score(s) in a subject or patient population. In these methods, the first composition containing an omega-3 oil may contain one or more (e.g., at least two, three, four, five, six, seven, eight, nine, or ten) absorption enhancers. In additional examples of these methods, the first or second composition may be administered (e.g., orally administered) once a day, twice a day, three times a day, four times a day, once every two days, once every three days, once every four days, once every five days, once every six days, and once a week). A variety of COX-1 inhibitors, COX-2 inhibitors, DMARDs, steroids, and TNF-α inhibitors that may be included in the first composition are described above. A variety of antihistamines are known in the art and include, without limitation, tricyclic antihistamines (e.g., doxepin and imipramine) and non-tricyclic antihistamines (e.g., diphenhydramine and triprolidine). In various examples of these methods, the first composition and the second composition may be co-administered or administered at different times (the first composition is administered to the subject prior to the administration of the second composition to the subject, or the second composition is administered to the subject prior to administration of the first composition to the subject).

The methods of the invention may result in a decrease (e.g., by at least 5%, 10%, 15%, 20%, 25%, 30%, 35%, 40%, 45%, 50%, 55%, 60%, 65%, 70%, 75%, 80%, 85%, 90%, 95%, or 99%) in pain (e.g., acute pain, neuropathic pain, and chronic pain) in a subject. The methods of the invention may also be used to decrease the pain associated with a variety of different disease states (e.g., rheumatoid arthritis, osteoarthritis, gingivitis, periodontal disease, asthma, chronic obstructive pulmonary disease, autoimmune diseases, irritable bowel syndrome, fibromyalgesia, leg pains, restless leg syndrome, and an allergic condition). The methods of the invention may result in a decrease (e.g., by at least 5%, 10%, 15%, 20%, 25%, 30%, 35%, 40%, 45%, 50%, 55%, 60%, 65%, 70%, 75%, 80%, 85%, 90%, or 95%) in the pain test score in one or more pain score tests (e.g., Alder Hey Triage Pain Score, Brief Pain Inventory (BPI), Dallas Pain Questionnaire, Dolorimeter Pain Index (DPI), Faces Pain Scale-Revised (FPS-R), Face Legs Arms Cry Consolability scale, McGill Pain Questionnaire (MPQ), Descriptor Differential Scale (DDS), Neck Pain and Disability Scale (NPAD), Numerical 11 point box (BS-11), Numeric Rating Scale (NRS-11), Roland-Morris Back Pain Questionnaire, Wong-Baker FACES Pain Rating Scale, Visual Analog Scale (VAS), and Disease Activity Score (DAS)). The methods of the invention may also result in at least a 2-fold (e.g., at least a 3-fold, 4-fold, or 5-fold) decrease in the time to optimal therapeutic effect (e.g., pain relief). In desirable embodiments, the subject may also experience dysphagia, whereby the provided compositions allow for greater ease of administration to achieve the therapeutic effect.

The methods of the invention may also allow for a decrease in the dosage of one or more analgesics, anti-inflammatory medications, or antihistamines (e.g., diclofenac, diflusinal, etodolac, fenoprofen, flurbiprofen, ibuprofen, indomethacin, ketoprofen, ketorolac, meclofenamate, mefenamic acid, meloxicam, nabumetone, naproxen, oxaprozin, phenylbutazone, piroxicam, sulindac, tolmetin, celecoxib, buprenorphine, butorphanol, codeine, hydrocodone, hydromorphone, levorphanol, meperidine, methadone, morphine, nalbuphine, oxycodone, oxymorphone, pentazocine, propoxyphene, tramadol, acetaminophen, ibuprofen, an antihistamine, and aspirin) administered to the subject. The methods of decreasing pain may further include the administration of one or more (e.g., at least two, three, or four) analgesics and/or one or more (e.g., at least two, three, or four) anti-inflammatory agent(s) (e.g., NSAID, DMARD, steroid, and TNF-α inhibitor) to the subject (e.g., diclofenac, diflusinal, etodolac, fenoprofen, flurbiprofen, ibuprofen, indomethacin, ketoprofen, ketorolac, meclofenamate, mefenamic acid, meloxicam, nabumetone, naproxen, oxaprozin, phenylbutazone, piroxicam, sulindac, tolmetin, celecoxib, buprenorphine, butorphanol, codeine, hydrocodone, hydromorphone, levorphanol, meperidine, methadone, morphine, nalbuphine, oxycodone, oxymorphone, pentazocine, propoxyphene, tramadol, acetaminophen, ibuprofen, aspirin, and an antihistamine) Additional analgesics, anti-inflammatory agents, and antihistamines (e.g., NSAIDs, DMARDs, steroids, TNF-α inhibitors, and antihistamines) that may be administered with one or more pharmaceutical compositions described herein are known in the art. In examples of these methods, the administration of a composition containing an omega-3 oil and at least one anti-inflammatory agent results in a synergistic decrease in at least one (e.g., at least two, three, four, or five) symptom of inflammation or an allergic condition or a synergistic decrease in at least one (e.g., at least two, three, four, or five) test pain score in the subject compared to the sum of the effect of the omega-3 oil alone and the effect of the anti-inflammatory agent(s) alone on the symptom(s) of inflammation or an allergic condition, or the test pain score(s) in a subject or patient population.

The methods of the invention may also be used to decrease (e.g., by at least 10%, 15%, 20%, 25%, 30%, 35%, 40%, 45%, 50%, 55%, 60%, 65%, 70%, 75%, 80%, 85%, 90%, 95%, or 99%) inflammation or one or more (e.g., at least two, three, four, or five) symptoms of inflammation or an allergic condition in a subject. The methods of the invention may also be used to decrease the inflammation associated with a variety of different disease states (e.g., cancer, viral infection, rheumatoid arthritis, osteoarthritis, Crohn's disease, liver disease, inflammatory heart disease, kidney disease, gastritis, gingivitis, periodontal disease, asthma, chronic obstructive pulmonary disease (COPD), autoimmune diseases, irritable bowel syndrome, neuropathic pain, fibromyalgesia, neuropathic pain, leg pains, neuropathic pain, restless leg syndrome, diabetic neuropathy, and an allergic condition). The methods of the invention may result in a decrease (e.g., by at least 5%, 10%, 15%, 20%, 25%, 30%, 35%, 40%, 45%, 50%, 55%, 60%, 65%, 70%, 75%, 80%, 85%, 90%, or 95%) in COX-1 and/or COX-2 activity relative to the COX-1 and/or COX-2 activity in the subject prior to treatment or the COX-1 and/or COX-2 activity in a subject or patient population not receiving treatment. The methods of the invention may also result in a decrease (e.g., by at least 5%, 10%, 15%, 20%, 25%, 30%, 35%, 40%, 45%, 50%, 55%, 60%, 65%, or 70%) in white blood cell count relative the white blood cell count in the subject prior to treatment or the white blood cell count in a subject or a patient population not receiving treatment. The methods of the invention may also result in a decrease (e.g., by at least 5%, 10%, 15%, 20%, 25%, 30%, 35%, 40%, 45%, 50%, 55%, 60%, 65%, or 70%) in C-reactive protein, interleukin-6, and/or TNF-alpha levels, swelling, and/or pain in a subject relative to the amount of C-reactive protein, interleukin-6, and/or TNF-alpha levels, swelling, and/or pain observed in the subject prior to treatment or the amount of C-reactive protein, interleukin-6, and TNF-α levels, swelling, and/or pain observed in a subject or a patient population not receiving treatment. The methods of treatment may also result in a decrease (e.g., by at least 5%, 10%, 15%, 20%, 25%, 30%, 35%, 40%, 45%, 50%, 55%, 60%, 65%, or 70%) in erythrocyte sedimentation rate in a subject compared to the erythrocyte sedimentation rate in the subject prior to treatment or the erythrocyte sedimentation rate in a subject or a patient population not receiving treatment. In one example of the methods for decreasing pain or inflammation, the subject is administered one or more (e.g., at least two, three, four, or five) pharmaceutical compositions of the invention containing rosemary oil and glucosamine. The methods of the invention may also result in at least a 2-fold (e.g., at least a 3-fold, 4-fold, or 5-fold) decrease in the time to optimal therapeutic effect.

The provided methods may also allow for a decrease in the dosage of one or more (e.g., at least two, three, four, or five) anti-inflammatory medications (e.g., NSAIDs, DMARDs, steroids, and TNF-α inhibitors) and/or antihistamines administered to a subject. The methods for decreasing inflammation may further include the administration of one or more (e.g., at least two, three, or four) analgesics and/or one or more (e.g., at least two, three, or four) anti-inflammatory medications to the subject (e.g., NSAIDs, DMARDs, steroids, and TNF-α inhibitors). Additional analgesic and anti-inflammatory medications that may be co-administered with one or more of the provided pharmaceutical compositions are known in the art. The effectiveness of all the above methods of treatment may be measured by a physician using methods known in the art.

In the above methods, one or more pharmaceutical compositions of the invention may be administered co-extensively (overlapping bioactive periods) or non-extensively (non-overlapping bioactive periods). For example, a first composition containing an omega-3 oil may be administered co-extensively with a second composition containing one or more (e.g., at least two, three, four, or five) anti-inflammatory agents. The combined amount of EPA and DHA present in a single dose of the provided pharmaceutical agents may be at least 2.5 g (e.g., at least 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, 5.0 g, 5.1 g, 5.2 g, 5.3 g, 5.4 g, 5.5 g, 5.6 g, 5.7 g, 5.8 g, 5.9 g, or 6.0 g) in a volume of at least 5.0 mL (e.g., at least 5.5 mL, 6.0 mL, 6.5 mL, 7.0 mL, 7.5 mL, 8.0 mL, 8.5 mL, 9.0 mL, 9.5 mL, 10.0 mL, 10.5 mL, 11.0 mL, 11.5 mL, 12.0 mL, 12.5 mL, 13.0 mL, 13.5 mL, 14.0 mL, 14.5 mL, or 15.0 mL). The amount of an anti-inflammatory agent present in a single dose of the provided pharmaceutical agents may be between 0.1 mg and 6 g, 0.1 mg and 5 g, 0.1 mg and 4.5 g, 0.1 mg and 5.0 g, 100 mg and 5.0 g, 500 mg and 5.0 g, 1.0 g and 5.0 g, 2.0 g and 5.0 g, 3.0 g and 4.5 g, and 3.0 g and 4.0 g. In these methods, the one or more (e.g., at least two, three, four, or five) pharmaceutical compositions of the invention may be administered with one or more (e.g., at least two, three, four, or five) additional therapeutic agents including, but not limited to, one or more (e.g., at least two, three, four, or five) anti-inflammatory agents (e.g., NSAID(s) (e.g., COX-1 and COX-2 inhibitors), DMARD(s), steroids, and TNF-α inhibitors), one or more (e.g., at least two, three, four, or five) analgesics, one or more (e.g., at least two, three, four, or five) triglyceride- or LDL cholesterol-lowering agents (e.g., statins), one or more (e.g., at least two, three, four, or five) cardiovascular disease medications (e.g., diuretics, angiotensin-converting enzyme (ACE) inhibitors, beta blockers, blood thinning medications (e.g., aspirin), HDL/LDL- or triglyceride-modifying drugs (e.g., statins, niacin, niacin derivatives, agents that have niacin-like mechanism of action, and fibrates (e.g., fibric acid or fenofibrate)), one or more (e.g., at least two, three, four, or five) diabetes medications (e.g., insulin (e.g., lys-pro or short-acting insulin, intermediate-acting insulin, or long-acting insulin), sulfonylureas, biguanides, alpha-glycosidase inhibitors, thiazolidinediones, and meglitinides), and one or more (e.g., at least two, three, four, or five) gastrotoxic, nephrotoxic, or hepatotoxic pharmaceutical agents. For example, the administered compositions may contain a statin and a fibrate or a statin combined with a fibrate and a niacin-like compound. The one or more additional therapeutic agents may be co-administered with the one or more pharmaceutical compositions provided by the invention (e.g., in the same or separate dosage forms). In additional examples of the provided methods, the one or more additional therapeutic agents are administered following the administration of the one or more pharmaceutical compositions of the invention to the subject (e.g., within 5 minutes, 10 minutes, 15 minutes, 20 minutes, 25 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 1 day, 2 days, 3 days, 5 days, and 1 week). In additional examples of the methods, the one or more pharmaceutical compositions provided by the invention may be administered following the administration of the one or more additional therapeutic agent(s) to the subject (e.g., within 5 minutes, 10 minutes, 15 minutes, 20 minutes, 25 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 1 day, 2 days, 3 days, 5 days, and 1 week). In these methods, the one or more pharmaceutical compositions and the one or more additional therapeutic agents may be administered co-extensively (overlapping bioactive periods) or non-extensively (non-overlapping bioactive periods).

The amount of one or more additional pharmaceutical compositions (e.g., anti-inflammatory agent (e.g., NSAID, DMARD, steroid, and TNF-α inhibitor) and gastrotoxic, nephrotoxic, or hepatotoxic pharmaceutical agent) that may be co-administered to a subject per dose may be between 0.1 mg and 6 g, 0.1 mg and 5 g, 0.1 mg and 4.5 g, 0.1 mg and 5.0 g, 100 mg and 5.0 g, 500 mg and 5.0 g, 1.0 g and 5.0 g, 2.0 g and 5.0 g, 3.0 g and 4.5 g, and 3.0 g and 4.0 g.

The one or more pharmaceutical compositions provided by the invention and the one or more additional therapeutic agents may be administered to a subject once a day, twice a day, three times a day, four times a day, once a week, twice a week, three times a week, four times a week, five times a week, six times a week, seven times a week, bi-weekly, tri-weekly, or monthly. For example, the one or more pharmaceutical compositions of the invention and the one or more additional therapeutic agents may be orally administered to a subject once, twice, three times, or four times a day. The one or more pharmaceutical compositions of the invention and the one or more additional therapeutic agents may be administered via the same route of administration (e.g., oral administration) or via different routes of administration (e.g., oral and parenteral administration). The one or more pharmaceutical compositions of the invention and the one or more additional therapeutic agents may be formulated for any known route of administration, including oral, intravenous, intraarterial, intraocular, intranasal, intramuscular, and subcutaneous administration. The therapeutically effective dose of the one or more pharmaceutical compositions of the invention and the one or more additional therapeutic agents may be determined by a skilled physician using methods known in the art.

Methods of Decreasing Gastrotoxicity, Nephrotoxicity, or Hepatotoxicity

The invention further provides methods for decreasing at least one symptom of gastrotoxicity, nephrotoxicity, or hepatotoxicity induced by one or more (e.g., at least two, three, four, five, six, seven, eight, nine, or ten) pharmaceutical agents requiring the steps of administering to a subject at least one (e.g., at least two, three, four, five, or six) composition comprising omega-3 oil and at least one (e.g., at least two, three, four, five, or six) pharmaceutical agent to the subject, whereby the administering results in at least a 10% decrease (e.g., at least 15%, 20%, 25%, 30%, 35%, 40%, 45%, 50%, 55%, 60%, 65%, 70%, 75%, 80%, 85%, 90%, or 95% decrease) in the one or more symptoms of gastrotoxicity, hepatotoxicity, or nephrotoxicity observed when the pharmaceutical agent(s) are administered alone. In desirable embodiments, the subject may also experience dysphagia, whereby the provided compositions allow for greater ease of administration to achieve a therapeutic effect.

A physician may monitor gastrotoxicity, nephrotoxicity, or hepatotoxicity by measuring one or more of the following symptoms in a subject. Non-limiting examples of symptoms of gastrotoxicity include: nausea, vomiting, loss of appetite, bloating, belching, ulcers, stomach pains, occult blood in feces, and weight loss (compared to a control subject or patient population). Non-limiting examples of symptoms of hepatotoxicity include: increased (e.g., by at least 10%, 15%, 20%, 25%, 30%, 35%, 40%, 45%, 50%, 55%, 60%, 65%, 70%, 75%, 80%, 85%, 90%, or 95%) aspartate aminotransferase levels in the blood; increased (e.g., by at least 10%, 15%, 20%, 25%, 30%, 35%, 40%, 45%, 50%, 55%, 60%, 65%, 70%, 75%, 80%, 85%, 90%, or 95%) alkaline phosphatase levels in the blood; increased (e.g., by at least 10%, 15%, 20%, 25%, 30%, 35%, 40%, 45%, 50%, 55%, 60%, 65%, 70%, 75%, 80%, 85%, 90%, or 95%) alanine transaminase levels in the blood, increased (e.g., by at least 10%, 15%, 20%, 25%, 30%, 35%, 40%, 45%, 50%, 55%, 60%, 65%, 70%, 75%, 80%, 85%, 90%, or 95%) total bilirubin in the blood, increased (e.g., by at least 10%, 15%, 20%, 25%, 30%, 35%, 40%, 45%, 50%, 55%, 60%, 65%, 70%, 75%, 80%, 85%, 90%, or 95%) gamma-glutamyltransferase levels in the blood, jaundice, abdominal pain or swelling, bloody stool, chronic fatigue, nausea, loss of appetite, and hepatomegaly. Non-limiting examples of nephrotoxicity include: increased (e.g., by at least 10%, 15%, 20%, 25%, 30%, 35%, 40%, 45%, 50%, 55%, 60%, 65%, 70%, 75%, 80%, 85%, 90%, or 95%) urea nitrogen in the blood, increased (e.g., by at least 10%, 15%, 20%, 25%, 30%, 35%, 40%, 45%, 50%, 55%, 60%, 65%, 70%, 75%, 80%, 85%, 90%, or 95%) creatine levels in urine, increased (e.g., by at least 10%, 15%, 20%, 25%, 30%, 35%, 40%, 45%, 50%, 55%, 60%, 65%, 70%, 75%, 80%, 85%, 90%, or 95%) microalbumin in urine, nausea, vomiting, loss of appetite, and weakness (compared to a control subject or patient population).

These methods provide for a reduction by at least 10% (e.g., by at least 15%, 20%, 25%, 30%, 35%, 40%, 45%, 50%, 55%, 60%, 65%, 70%, 75%, 80%, 85%, 90%, or 95%) in at least one (e.g., at least two, three, four, or five) symptoms of gastrotoxicity, nephrotoxicity, or hepatotoxicity. Non-limiting examples of such a reduction include: a decrease (e.g., by at least 10%, 15%, 20%, 25%, 30%, 35%, 40%, 45%, 50%, 55%, 60%, 65%, or 70%) in aspartate aminotransferase levels in the blood; a decrease (e.g., by at least 10%, 15%, 20%, 25%, 30%, 35%, 40%, 45%, 50%, 55%, 60%, 65%, or 70%) in alkaline phosphatase levels in the blood; a decrease (e.g., by at least 10%, 15%, 20%, 25%, 30%, 35%, 40%, 45%, 50%, 55%, 60%, 65%, or 70%) in alanine transaminase levels in the blood, a decrease (e.g., by at least 10%, 15%, 20%, 25%, 30%, 35%, 40%, 45%, 50%, 55%, 60%, 65%, or 70%) in total bilirubin levels in the blood, a decrease (e.g., by at least 10%, 15%, 20%, 25%, 30%, 35%, 40%, 45%, 50%, 55%, 60%, 65%, or 70%) in gamma-glutamyltransferase levels in the blood, a decrease (e.g., by at least 10%, 15%, 20%, 25%, 30%, 35%, 40%, 45%, 50%, 55%, 60%, 65%, or 70%) in urea nitrogen in the blood, a decrease (e.g., by at least 10%, 15%, 20%, 25%, 30%, 35%, 40%, 45%, 50%, 55%, 60%, 65%, or 70%) in creatine levels in urine, a decrease (e.g., by at least 10%, 15%, 20%, 25%, 30%, 35%, 40%, 45%, 50%, 55%, 60%, 65%, or 70%) in microalbumin in urine, decreased jaundice, a reduction in abdominal pain or swelling, a reduction in bloody stool, reduced fatigue, reduced nausea or vomiting (e.g., frequency or periodicity), a decrease in loss of appetite, decreased bloating, decreased belching, decreased ulcers, decreased stomach pain, reduced occult blood in feces, and reduced hepatomegaly.

In these methods, the omega-3 oils included in the composition containing omega-3 oil may be obtained from a natural source, including, for example, cold water oily fish (e.g., salmon, tuna, herring, mackerel, anchovies, and sardines), pollock, cod, catfish, flounder, grouper, halibut, mahi mahi, orange roughy, red snapper, shark, swordfish, tilefish, plankton, algae, krill, green-lipped mussel, chia seeds, kiwifruit seeds, perilla seeds, flax seeds, lingonberry seeds, camelina seeds, purslane seeds, black raspberry seeds, hemp seeds, butternut, walnuts, pecan nuts, and hazel nuts. The omega-3 oil included in the pharmaceutical compositions may be high grade (e.g., at least 70%, 75%, 80%, 85%, 90%, 91%, 92%, 93%, 94%, 95%, 96%, 97%, 98%, or 99% pure). In one example, the high grade omega-3 oil used in the pharmaceutical compositions is OmegaMaine omega-3 oils. In additional non-limiting examples of the pharmaceutical compositions, the omega-3 oil is at least 25% (e.g., at least 30%, 35%, 40%, 45%, 50%, 55%, 65%, 70%, 75%, 80%, 85%, 90%, or 95%) of the composition's total mass. In one implementation of the invention, at least 10% (e.g., at least 15%, 20%, 25%, 30%, 35%, 40%, 45%, or 50%) of the omega-3 oil in the composition is in solution and at least 50% (e.g., at least 55%, 60%, 65%, 70%, 75%, 80%, 85%, 90%, or 95%) of the omega-3 oil in the composition is in stable suspension form. The omega-3 oil is typically a mixture of one or more (e.g., at least two, three, or four) omega-3 fatty acids, including EPA, DHA, or a combination thereof.

The combined amount of EPA and DHA present in a single dose of the omega-3 oil-containing compositions may be at least 2.5 g (e.g., at least 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, 5.0 g, 5.1 g, 5.2 g, 5.3 g, 5.4 g, 5.5 g, 5.6 g, 5.7 g, 5.8 g, 5.9 g, or 6.0 g) in a volume of at least 5.0 mL (e.g., at least 5.5 mL, 6.0 mL, 6.5 mL, 7.0 mL, 7.5 mL, 8.0 mL, 8.5 mL, 9.0 mL, 9.5 mL, 10.0 mL, 10.5 mL, 11.0 mL, 11.5 mL, 12.0 mL, 12.5 mL, 13.0 mL, 13.5 mL, 14.0 mL, 14.5 mL, or 15.0 mL).

The gastrotoxic, nephrotoxic, or hepatotoxic pharmaceutical agents administered in these methods may include any known synthetic or natural agent that is known to induce gastrotoxicity, nephrotoxicity, or hepatotoxicity in a subject following administration to a subject (e.g., following at administration for at least 1 day, 1 week, two weeks, three weeks, one month, two months, three months, four months, five months, six months, seven months, eight months, nine months, ten months, eleven months, one year, two years, three years, four years, and five years) and may have a molecular weight between 100 g/mole and 800 g/mole (e.g., between 100 g/mole and 400 g/mole, between 400 g/mole and 800 g/mole, between 200 g/mole and 700 g/mole, and between 300 g/mole and 600 g/mole), a log P value greater than 2 (e.g., greater than 2.5, greater than 3.0, greater than 3.5, and greater than 4.0), and/or a melting point of below 200° C. (e.g., below 180° C., below 160° C., and below 140° C.). These pharmaceutical agents may be administered to decrease one or more symptoms (e.g., pain and inflammation) of any disease state (e.g., cancer, viral infection (e.g., HIV), arthritis (e.g., rheumatoid arthritis and osteoarthritis), diabetic neuropathy, autoimmune diseases, Crohn's disease, gingivitis, periodontal disease, liver disease, inflammatory heart disease, kidney disease, gastritis, peripheral vascular pain, irritable bowel syndrome, chronic pulmonary diseases (e.g., asthma and chronic obstructive pulmonary disease), leg pains, fibromyalgesias, restless leg syndrome, and an allergic condition (e.g., contact dermatitis and seasonal allergies). Non-limiting examples of gastrotoxic, nephrotoxic, or hepatotoxic pharmaceutical agents that may be included in the compositions of the invention include: acetaminophen, ibuprofen, alpha-methyldopa, amiodarone, carbamazepine, chlorzoxazone, dantrolene, diclofenac, fluconazole, ketoconazole, flutamide, hydralazine, ibuprofen, imuran, azathioprine, isoniazid, ketek, long-acting nicotinic acid, zafirlukast accolade, zileuton, methotrexate, nitrofurantoin, perihexilene maleate, phenylbutazone, phenytoin, pravastin, fluvastatin, simavastatin, lovastatin, quinidine, rifampin, septra, bactrim, tacrine, tasmar, ticlid, troglitzone, clofarabine, pemetrexed, aldesleukin, fenofibrate, gemfibrozil, clofibrate, fenofibric acid, indomethacin, methotrexate sodium, ibuprofen, naproxen sodium, meloxicam, stavudine, didanosine, zidovudine, nevirapine, ritonavir, cisplatin, carboplatin, carmustine, mitomycin, amphotericin B, gentamycin, vancomycin, angiotensin-converting enzyme (ACE) inhibitors, furosemide, an antihistamine, and HDL/LDL- or triglyceride-modulating agents (e.g., a fibrate, statin, niacin, or niacin derivative). The amount of one or more gastrotoxic, nephrotoxic, and hepatotoxic pharmaceutical agent(s) present in a single dose of the provided pharmaceutical agents may be between 0.1 mg and 6 g, 0.1 mg and 5 g, 0.1 mg and 4.5 g, 0.1 mg and 5.0 g, 100 mg and 5.0 g, 500 mg and 5.0 g, 1.0 g and 5.0 g, 2.0 g and 5.0 g, 3.0 g and 4.5 g, and 3.0 g and 4.0 g.

The compositions used in these methods may also include one or more (e.g., at least two, three, four, five, six, seven, eight, nine, or ten) absorption enhancers in order to increase the rate of absorption of the omega-3 oil or the hepatotoxic, nephrotoxic, or hepatotoxic pharmaceutical agent(s). Absorption enhancers included in the compositions may be any solvent or agent that enhances the absorption rate of omega-3 oils and/or the gastrotoxic, nephrotoxic, or hepatotoxic pharmaceutical agent(s) in a subject (e.g., a human). Non-limiting examples of absorption enhancers that may be included in the compositions are: ethanol, vitamin E, a polyethylene glycol, a Tween surfactant (e.g., Tween-80, Tween-60, Tween-40, and Tween-20), cremophor, Span 20, Span 80, labrasol, olive oil, arginine, citrulline, phosphatidylserine, phosphatidylcholine, phosphatidic acid, phosphoinositol, phosphatidylethanolamine, polytocopherol, medium chain triglycerides (MCTs), sodium lauryl sulfate, natural fish oil, palmitic monoglycerides or diglycerides, capric monoglycerides or diglycerides, amides of intermediate (C-8 to C-12) fatty acids (e.g., lauryl acid), and amides of long chain (C-13 to C-24) fatty acids (e.g., palmitic acid). In examples of these compositions, the one or more absorption enhancer(s) are less than 30% (e.g., less than 25%, 20%, 15%, 10%, or 5%) of the composition's total mass.

Non-limiting examples of the compositions used in these methods contain vitamin E as an absorption enhancer and rosemary oil. In additional examples of the compositions used in these methods, one or more of natural fish oil, palmitic monoglycerides or diglycerides, or capric monoglycerides or diglycerides are included as absorption enhancers. In other examples of these methods, the absorption enhancers present in the composition(s) (e.g., between 1% and 10% of the composition's total mass) include one or more of: phosphatidylinositol, phosphatidylserine, phosphatidylcholine, phosphatidylethanolamine, and phosphatidic acid (e.g., phosphatidylcholine, phosphatidylserine, and phosphatidic acid). Additional examples of the compositions used in these methods may contain (by weight) 1% to 5% of polytocopherol, 1% to 5% arginine or citrulline, and/or 1% to 10% medium chain triglycerides (e.g., coconut oil) as absorption enhancer(s).

Examples of the omega-3 oil-containing compositions that may be used in these methods may contain (by weight): 60% to 80% of omega-3 oil; 0.5% to 5% rosemary oil; 1% to 10% mixture of phosphatidylserine, phosphatidylcholine, and phosphatidic acid; 1% to 5% polytocopherol; 1% to 5% arginine or citrulline; and/or 1% to 10% medium chain triglycerides.

Additional examples of the omega-3 oil-containing compositions that may be used in these methods may contain (by weight): 60% to 80% omega-3 oil; 0.5% to 5% rosemary oil; 1% to 10% mixture of phosphatidylserine, phosphatidylcholine, and phosphatidic acid; 1% to 5% polytocopherol; and 1% to 5% arginine or citrulline; and/or 1% to 20% anti-inflammatory agent(s) (e.g., NSAID(s) or DMARD(s)).

The one or more compositions containing omega-3 oil and/or the one or more gastrotoxic, nephrotoxic, or hepatotoxic pharmaceutical agent(s) may be administered (e.g., orally) to a subject once a day, twice a day, three times a day, four times a day, once a week, twice a week, three times a week, four times a week, five times a week, six times a week, seven times a week, bi-weekly, tri-weekly, or monthly. For example, the one or more compositions containing omega-3 oil and the one or more gastrotoxic, nephrotoxic, or hepatotoxic pharmaceutical agents may be orally administered to a subject once, twice, three times, or four times a day. The compositions and pharmaceutical agents may be administered via the same route of administration (e.g., oral administration) or via different routes of administration (e.g., oral and parenteral administration). The one or more omega-3 oil-containing compositions and the one or more gastrotoxic, nephrotoxic, or hepatotoxic pharmaceutical agents may be formulated for any known route of administration, including oral, intravenous, intraarterial, intraocular, intranasal, intramuscular, and subcutaneous administration. The therapeutically effective dose of the omega-3 oil-containing compositions and the one or more gastrotoxic, nephrotoxic, or hepatotoxic pharmaceutical agents may be determined by a skilled physician using methods known in the art.

In various examples of these methods, the composition(s) containing omega-3 oil may be administered to the subject prior to administering the gastrotoxic, nephrotoxic, or hepatotoxic pharmaceutical agent(s) (e.g., within 5 minutes, 10 minutes, 15 minutes, 20 minutes, 25 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 1 day, 2 days, 3 days, 5 days, and 1 week). In other examples of these methods, the gastrotoxic, nephrotoxic, or hepatotoxic pharmaceutical agent(s) may be administered to the subject prior to administering the composition(s) containing omega-3 oil (e.g., within 5 minutes, 10 minutes, 15 minutes, 20 minutes, 25 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 1 day, 2 days, 3 days, 5 days, and 1 week). In another version of these methods, the composition(s) containing omega-3 oil and the gastrotoxic, nephrotoxic, and hepatotoxic pharmaceutical agents are administered to the subject at the same time.

The effectiveness of all the above methods of treatment may be measured by a physician using methods known in the art. In one example, the methods allow for an increased dosage (e.g., by at least 10%, 15%, 20%, 25%, 30%, 35%, 40%, 45%, 50%, 55%, 60%, 65%, 70%, 75%, 80%, 85%, 90%, or 95%) of one of more one or more (e.g., at least two, three, or four) gastrotoxic, nephrotoxic, or hepatotoxic pharmaceutical agent(s) to be administered to a subject (e.g., without an adverse effect or a reduction in the severity or periodicity of an adverse effect (e.g., gastrotoxicity, nephrotoxicity, or hepatotoxicity)) or allows for an increased duration (e.g., by at least 10%, 15%, 20%, 25%, 30%, 35%, 40%, 45%, 50%, 55%, 60%, 65%, 70%, 75%, 80%, 85%, 90%, or 95%) of therapeutic treatment using one or more (e.g., at least two, three, or four) gastrotoxic, nephrotoxic, or hepatotoxic pharmaceutical agent(s) (e.g., due to a reduction in gastrotoxicity, nephrotoxicity, or hepatotoxicity).

Methods for Decreasing Inflammation and Allergic Conditions in Companion Animals The invention further provides methods of decreasing (e.g., by at least 10%, 15%, 20%, 25%, 30%, 35%, 40%, 50%, 60%, 70%, or 80%) one or more (e.g., two, three, four, or five) symptoms of inflammation or an allergic condition in a companion animal (e.g., a cat, dog, bird, or horse) by administering one or more (e.g., two, three, four, or five) of the compositions of the invention. The one or more symptoms of inflammation or an allergic condition may be followed by a veterinarian in the animal. For example, inflammation may monitored by a veterinarian by measuring one of more of the following in an animal: increased (e.g., by at least 5%, 10%, 15%, 20%, 25%, 30%, 35%, 40%, 45%, 50%, 55%, 60%, 65%, 70%, 75%, 80%, 85%, 90%, or 95%) COX-1 and/or COX-2 activity, increased (e.g., by at least 5%, 10%, 15%, 20%, 25%, 30%, 35%, 40%, 45%, 50%, 55%, 60%, 65%, 70%, 75%, 80%, 85%, 90%, or 95%) white blood cell count, increased (e.g., by at least 5%, 10%, 15%, 20%, 25%, 30%, 35%, 40%, 45%, 50%, 55%, 60%, 65%, 70%, 75%, 80%, 85%, 90%, or 95%) C-reactive protein, interleukin-6, and/or TNF-alpha levels, swelling, pain, and increased (e.g., by at least 5%, 10%, 15%, 20%, 25%, 30%, 35%, 40%, 45%, 50%, 55%, 60%, 65%, 70%, 75%, 80%, 85%, 90%, or 95%) erythrocyte sedimentation rate. An allergic condition may be monitored by a veterinarian in an animal by following one or more of the following symptoms in an animal: nasal congestion, sneezing, runny nose, watery eyes, swollen eyes, itchy nose, itchy skin, itchy eyes, tingling mouth, swelling of the lips, mouth, or throat, hives, anaphylaxis, rash, wheezing, loss of or decreased mobility, or increased sleeping. Desirably, the administration of the composition of the invention results in a synergistic decrease in one or more symptoms of inflammation or an allergic condition compared to the sum of the effects of the omega-3 oil and the anti-inflammatory agent on the one or more symptoms of inflammation or an allergic condition when administered alone.

The compositions of the invention may be administered to the animal in a liquid form (e.g., orally administered). Desirably, the composition is administered in a liquid form as a supplement to the animal's normal food source (e.g., dry food). The compositions of the invention may be formulated in all the various ways described herein. In addition, the compositions may be administered to the animal as described above for other subjects (e.g., human subjects). For example, one or more composition(s) of the invention may be administered to an animal once a day (e.g., by oral administration, such as oral administration in the form of a liquid). The combined amount of EPA and DHA present in a single dose of the omega-3 oil-containing compositions may be at least 0.2 g (e.g., at least 0.3 g, 0.4 g, 0.5 g, 0.6 g, 0.7 g, 0.8 g, 0.9 g, 1.0 g, 1.1 g, 1.2 g, 1.3 g, 1.4 g, 1.5 g, 1.6 g, 1.7 g, 1.8 g, 1.9 g, 2.0 g, 2.5 g, 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, 5.0 g, 5.1 g, 5.2 g, 5.3 g, 5.4 g, 5.5 g, 5.6 g, 5.7 g, 5.8 g, 5.9 g, or 6.0 g) in a volume of at least 0.3 mL (e.g., at least 0.5 mL, 1.0 mL, 1.5 mL, 2.0 mL, 2.5 mL, 3.0 mL, 3.5 mL, 4.0 mL, 4.5 mL, 5.0 mL, 5.5 mL, 6.0 mL, 6.5 mL, 7.0 mL, 7.5 mL, 8.0 mL, 8.5 mL, 9.0 mL, 9.5 mL, 10.0 mL, 10.5 mL, 11.0 mL, 11.5 mL, 12.0 mL, 12.5 mL, 13.0 mL, 13.5 mL, 14.0 mL, 14.5 mL, or 15.0 mL).

As described above, the anti-inflammatory agent in the provided compositions may be a natural anti-inflammatory agent (e.g., glucosamine or a herbal-based oil). The anti-inflammatory agent(s) in the composition may also be a COX-1 inhibitor, a COX-2 inhibitor, a DMARD, a TNF-α inhibitor, and/or an antihistamine (e.g., a tricyclic antihistamine or a non-tricyclic antihistamine), as described herein.

Additional examples of these methods may further include administering to the animal one or more (e.g., two, three, four, or five) additional compositions containing an anti-inflammatory agent (e.g., an antihistamine, a NSAID, and a DMARD). Desirably, the above methods result in at least a 5% reduction (e.g., at least 10%, 15%, 20%, 25%, 30%, 35%, 40%, 45%, 50%, 55%, 60%, 65%, 70%, or 80% reduction) in COX-1 and/or COX-2 activity, at least a 5% reduction (e.g., at least 10%, 15%, 20%, 25%, 30%, 35%, 40%, 45%, or 50% reduction) in white blood cell count, at least a 5% reduction (e.g., at least 10%, 15%, 20%, 25%, 30%, 35%, 40%, 45%, or 50% reduction) in C-reactive protein levels, at least a 5% reduction (e.g., at least 10%, 15%, 20%, 25%, 30%, 35%, 40%, 45%, or 50% reduction) in interleukin-6 levels, at least a 5% reduction (e.g., at least 10%, 15%, 20%, 25%, 30%, 35%, 40%, 45%, or 50% reduction) in TNF-α levels, or at least a 5% decrease (e.g., at least 10%, 15%, 20%, 25%, 30%, 35%, 40%, 45%, 50%, 55%, 60%, 65%, 70%, 75%, or 80% decrease) in the severity of one or more of the following symptoms: nasal congestion, sneezing, runny nose, watery eyes, swollen eyes, itchy nose, itchy skin, itchy eyes, tingling mouth, swelling of the lips, mouth, or throat, hives, anaphylaxis, rash, wheezing, loss of or decreased mobility, or increased sleeping.

The one or more pharmaceutical compositions provided by the invention and the one or more additional therapeutic agents may be administered to an animal once a day, twice a day, three times a day, four times a day, once a week, twice a week, three times a week, four times a week, five times a week, six times a week, seven times a week, bi-weekly, tri-weekly, or monthly. For example, the one or more pharmaceutical compositions of the invention and the one or more additional therapeutic agents may be orally administered to the animal once, twice, three times, or four times a day. The one or more pharmaceutical compositions of the invention and the one or more additional therapeutic agents may be administered via the same route of administration (e.g., oral administration) or via different routes of administration (e.g., oral and parenteral administration). The one or more pharmaceutical compositions of the invention and the one or more additional therapeutic agents may be formulated for any known route of administration, including oral, intravenous, intraarterial, intraocular, intranasal, intramuscular, and subcutaneous administration. The therapeutically effective dose of the one or more pharmaceutical compositions of the invention and the one or more additional therapeutic agents may be determined by a skilled veterinarian using methods known in the art.

EXAMPLES

The features and other details of the invention will now be more particularly described and pointed out in the following examples describing preferred techniques and experimental results. These examples are provided for the purpose of illustrating the invention and should not be construed as limiting.

Example 1

Compositions Containing Omega-3 Oil Mediate a Decrease in Inflammation in Humans with Established Inflammation A clinical study was performed to determine whether a composition containing omega-3 oil would have anti-inflammatory activity in subjects having established inflammation. In this study, fifty-eight patients with established and stable inflammatory pain, who were taking prescribed medications to control pain symptoms, were recruited via professional independent compounding pharmacies to participate in a 3-month long study. This study was designed to: (1) determine if a high dose of liquid omega-3 oil (OmegaMaine omega-3 oil) would reduce the intensity of pain resulting from inflammation in a period of 30 days or less; (2) determine if a clinical benefit could be maintained throughout the dosing period of 90 days; (3) determine if patients would volunteer, without outside encouragement, to stop taking their prescribed medications and control their pain using the omega-3 containing composition alone; and (4) determine if symptoms of gastric pain and nausea were decreased in patients receiving the omega-3 oil-containing composition.

At entry, patients were asked to score their pain on a Visual Analog Scale (1-10), where 8 or above indicates severe pain, 5-8 indicates moderate pain, and 3-5 indicates mild pain. All patients that signed a patient consent form received free product during the course of the 90-day study, and a $100 gift certificate if the study protocol was completed. Patients in the study were administered 2 teaspoons (10 mL) of OmegaMaine omega-3 oil once a day (containing minimally 3.5 g of combined EPA and DHA). A clinical monitor called each patient bimonthly to ensure compliance with the protocol and to ask if there were any adverse experiences with the omega-3 oil-containing composition.

The demographics of the study group were as follows: 65% were women, 35% were men; the average age of the whole group was 53; 50% of the study group had allergies; 78% of the study group were on prescribed medications; 81% of the study group augmented their medications with natural product remedies; 25% of the study group had some form of cardiovascular disease (hypertension, high low density lipoprotein (LDL) cholesterol levels, high triglycerides, and kidney disease); 100% of the study group had joint pain and inflammation; 49% of the study group suffered from generalized inflammation/fibromyalgia; 34% of the study group has been diagnosed with rheumatoid arthritis; and the study group had experienced chronic pain for an average period of 11 years.

TABLE 1

| Month | Severity Classification | % Reduction in Pain |
|---|---|---|
| Month 1 | Mild | 43% |
| Month 1 | Moderate | 26% |
| Month 1 | Severe | 40% |
| Month 2 | Mild | 43% |
| Month 2 | Moderate | 39% |
| Month 2 | Severe | 39% |
| Month 3 | Mild | 43% |
| Month 3 | Moderate | 49% |
| Month 3 | Severe | 49% |

Additional analysis indicated that 31% of the patients in the study self-elected to stop taking all other anti-inflammatory medications. These other anti-inflammatory medications included over-the-counter products, such as naproxen and ibuprofen, prescription products, such as celebrex, diclofenac, statins, niacin, and natural products, such as glucosamine. The study results indicate that the omega-3 oil-containing composition resulted in a significant decrease in pain within 1-month of dosing and remained constant in successive months of dosing. The continued relief from pain during the successive months of dosing strongly indicates that the observed effect was not a placebo effect. In those patients (25%) that experienced gastric pain as a result of anti-inflammatory drug therapy, the gastric pain experienced was greatly reduced (patient diary notation).

Example 2

Omega-3 Oil-Containing Compositions Decrease Inflammation in Humans with Gingivitis and/or Periodontal Disease Additional experiments were performed to determine whether an omega-3 oil-containing composition could decrease one or more symptoms of inflammation (e.g., bleeding of gums on probing, redness, number of bleeding sites, and probing depth) in patients having gingivitis and/or periodontal disease. In this study, twenty patients diagnosed with gingivitis or periodontitis by their dentists were enrolled in a 3-month study. Each patient was administered 3.5 grams of combined EPA and DHA a day (i.e., administered as 10 mL of OmegaMaine omega-3 oil). Bleeding on dental probing, redness, number of bleeding sites, and bleeding on probing were assessed before entering the study and after the completion of the study. After 3-months the patients were again evaluated by their dentist using the same parameters listed above. Throughout the study, patients were encouraged to brush and floss their teeth several times daily.

TABLE 2

| | Baseline | After 3-mo. of Omega-3 Oil | % Change |
|---|---|---|---|
| Bleeding on Probing | 6.3 | 4.6 | −40 |
| Redness | 4.2 | 3.4 | −19 |
| Bleeding Sites | 4.6 | 2.7 | −40 |
| Probing Depth (mm) | 7.0 | 4.0 | −57 |

These data demonstrate a significant reduction in four different symptoms of inflammation following daily administration of an omega-3 oil-containing composition (3.5 g of combined DHA and EPA/day) for 3 months in patients having gingivitis and/or periodontal disease. For patients suffering gingivitis, high dose liquid omega-3 oil in the form of OmagaMaine omega-3 oil reduces all symptoms of gingivitis, improves gum health, and delays or eliminates the need for aggressive dental procedures.

Example 3

Omega-3 Oil Containing Compositions Elicit a Decrease in Pain in Human Subjects

An additional set of experiments was performed to determine the affect of the dosage of omega-3 oil-containing compositions on the treatment of pain in humans. This study was performed using the same protocol as described in Example 1. The patients in group 1 were administered 2, 5-mL doses of OmegaMaine omega-3 oil (containing 1.75 grams combined of DHA and EPA per 5 mL dose) per day (once in the morning and once at night). The patients in group 2 were administered a single 10-mL dose (containing 3.5 grams combined of DHA and EPA) per day. Group 3 was given a 3.5 g grams of combined DHA and EPA in a composition further containing surfactants and co-solvents (as described in Example 4).

TABLE 3

| Test Groups | % Inhibition of Pain |
|---|---|
| Group 1 | |
| Mild | −10 |
| Moderate | −15 |
| Severe | −12 |
| Group 2 | |
| Mild | −29 |
| Moderate | −26 |
| Severe | −23 |
| Group 3 | |
| Mild | −45 |
| Moderate | −49 |
| Severe | −49 |

These data indicate that a single dosage of 3.5 grams combined EPA and DHA per day results in greater reduction in pain than a twice daily administration of 1.75 grams combined EPA and DHA (group 1 vs. group 2). The data further indicate that the formulation of an omega-3 oil in one or more absorption enhancers (e.g., surfactants and co-solvents, as described in Example 4) increases the ability of the omega-3 oil-containing composition to decrease pain (group 1 vs. group 3). These data indicate that the inclusion of the one or more absorption enhancers in the composition administered to group 3 enhances the rate of omega-3 oil absorption in humans. The liquid compositions of omega-3 are in contrast to gel caps: a common formulation for omega-3 oils. As omega-3 gel caps have a dissolution step that proceeds absorption, they have a slower rate of absorption than liquid omega-3 oil formulations.

Example 4

High Dose Liquid Omega-3 Oils Increase Mobility of Companion Animals

Experiments were performed to determine whether administration of the provided compositions would increase mobility in companion animals (e.g., dogs and cats). Small animals age much faster than humans and suffer inflammatory disease by year 5 of their lives. Inflammation affects the joints, hips, and the general mobility of such small animals. In addition, contact dermatitis is an allergic response with an inflammatory component. These effects in a companion animal are noticeable to the owners based on the behavior of the animals. For example, companion animals experiencing inflammation and an allergic response often demonstrate lack of or decreased movement, excessive sleep, and a decreased ability to play as was common early (e.g., below year 2 or below year 1) in their life.

Cats (n=5) were given 2.5 mL (½ teaspoon) of OmegaMaine liquid omega-3 oil by adding directly to their food. Dogs (n=5) were given 5 mL (1 teaspoon) of OmegaMaine omega-3 oil by adding directly to their food. For reference, 5 mL of OmegaMaine omega-3 oil contains, minimally, 800 mg of EPA, and, minimally, 750 mg of DHA. Animals were scored on a scale of 1 to 10, where 10 was behavior like a kitten or a puppy and 1 was severe immobility. All animals in the test group average 8 years of age. Animals were evaluated prior to treatment and 2 weeks after daily treatment with OmegaMaine omega-3 oil (Table 4).

TABLE 4

| Species | Prior to Treatment | After Treatment | % Improvement |
| --- | --- | --- | --- |
| Cats | 2 | 7 | 350% |
| Dogs | 4 | 8 | 200% |

The above data demonstrate that administration of OmegaMaine omega-3 oil results in an improvement in companion animal motility. The further addition of glucosamine (1000 mg/kg) provided an additional therapeutic benefit to these animals (data not shown).

Example 5

Preparation of Omega-3 Oil-Containing Compositions

The currently available formulations of omega-3 oil make it difficult for patients to consistently take an amount of omega-3 oil sufficient to elicit a therapeutic effect. In order to increase the absorption rate and provide an improved formulation of omega-3 oil, a new method for formulating omega-3 oil is provided below.

Step 1. An omega-3 oil (e.g., derived from fish) is made more concentrated in DHA and EPA by decreasing the storage temperature from 38° F. to 36° F. for 12 hours. The 36° F. incubation causes the higher molecular weight fats and fatty acids to precipitate out of the solution. After 12 hours, the liquid oil (containing DHA and EPA) is separated from the solid fats by decantation. The temperature is then decreased from 36° F. to 34° F., and incubated at 34° F. for an additional 24 hours. The clarified liquid is then decanted. The resulting clarified liquid is enriched by 25-40% in combined EPA and DHA. The use of cold temperature centrifugation may also be used to accelerate this process, by accelerating the rate of precipitation of the higher molecular weight fats and fatty acids from the solution.

Step 2. The following absorption enhancers were added to the clarified solution yielded in step 1 (enriched for DHA and EPA by 30%). The order of addition of each of the absorption enhancers below is not critical. The absorption enhancers are not designed to exceed 30% of the composition's total mass. Absorption Enhancers Added:

| | |
| --- | --- |
| 17% | medium chain triglycerides (MCTs) (coconut oil) |
| 3% | rosemary oil |
| 5% | mixture of phosphatidylserine, phosphatidylcholine and phosphatidic acid |
| 3% | polytocopherol |
| 2% | arginine or citrulline |

Alternatively, if one or more additional pharmaceutical agents are added to the composition, the amount of MCTs in the composition may be reduced to 10%, and 7% of the one or more additional pharmaceutical agents may be added to the composition (e.g., 7% of an additional pharmaceutical agent dissolved in ethanol). For example, the additional pharmaceutical agent may be selected from an anti-inflammatory agent (e.g., a NSAID, DMARD, steroid, and TNF-α inhibitor) or a gastrotoxic, nephrotoxic, or hepatotoxic pharmaceutical agent, or a HDL/LDL- or triglyceride modifying drug (e.g., a fibrate, statin, niacin, or niacin derivative). The compositions provided by these methods may be clear or cloudy and should be thoroughly shaken before using.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A composition consisting essentially of 0.5%-5% rosemary oil and 60%-80% omega-3 oil, wherein the omega-3 oil is selected from the group consisting of herring oil, sardine oil, anchovy oil, and combinations thereof, and wherein the omega-3 oil has a combined amount of eicosapentaenoic acid and docosahexaenoic acid which is greater than 2.5 g in a volume of 5.0 mL omega-3 oil.

2. The composition of claim 1, wherein the rosemary oil is 3% of the composition.

3. The composition of claim 1, wherein the omega-3 oil is 70% of the composition.

4. The composition of claim 1, wherein the combined amount of eicosapentaenoic acid and docosahexaenoic acid is greater than 3.0 g in a volume of 5.0 mL omega-3 oil.

5. The composition of claim 1, wherein the combined amount of eicosapentaenoic acid and docosahexaenoic acid is greater than 3.1 g in a volume of 5.0 mL omega-3 oil.

6. The composition of claim 1, wherein the composition is a liquid.

7. The composition of claim 1 or 6, wherein the composition is formulated for oral administration.

* * * * *